(12) United States Patent
Bodurka

(10) Patent No.: US 12,023,286 B2
(45) Date of Patent: *Jul. 2, 2024

(54) SMART HOSPITAL HEADWALL SYSTEM

(71) Applicant: Stryker Corporation, Kalamazoo, MI (US)

(72) Inventor: Alexander Josef Bodurka, Schoolcraft, MI (US)

(73) Assignee: Stryker Corporation, Kalamazoo, MI (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/466,057

(22) Filed: Sep. 3, 2021

(65) Prior Publication Data

US 2021/0393461 A1 Dec. 23, 2021

Related U.S. Application Data

(63) Continuation of application No. 16/217,203, filed on Dec. 12, 2018, now Pat. No. 11,110,020.

(Continued)

(51) Int. Cl.
*H04B 7/15* (2006.01)
*A61G 7/05* (2006.01)
(Continued)

(52) U.S. Cl.
CPC .............. *A61G 7/0524* (2016.11); *A61G 7/05* (2013.01); *A61G 7/0506* (2013.01); *A61G 12/005* (2013.01); *G16H 40/40* (2018.01); *H04B 5/00* (2013.01); *H04B 5/48* (2024.01); *H04B 5/70* (2024.01); *H04B 5/72* (2024.01);
(Continued)

(58) Field of Classification Search
CPC .......... A61G 7/018; A61G 7/005; A61G 7/05; A61G 7/0524; A61G 12/00; H04B 5/02; H04B 5/0025; H04B 5/0031; H04B 12/005; H04L 17/12; G08B 5/22; G08B 5/222;
(Continued)

(56) References Cited

U.S. PATENT DOCUMENTS 8,392,747 B2 * 3/2013 Ferguson ............. A61B 5/7465
600/300
10,474,808 B2 * 11/2019 Huster ................. G06Q 10/063
(Continued)

*Primary Examiner* — Blane J Jackson
(74) *Attorney, Agent, or Firm* — Warner Norcross + Judd LLP

(57) ABSTRACT

A stationary communication unit is adapted to be mounted to a headwall of a healthcare facility and enable wireless communication between a patient support apparatus and a nurse call system. The unit also performs one or more additional functions, such as, but not limited to: determining when a healthcare worker enters/exits the room; determining when the patient support apparatus exits/enters the room; storing/retrieving medical device data associated with a patient; directing medical device data to one or more displays in the room; auto-updating, auto-retrieving, and/or auto-displaying data upon healthcare worker entry into the room; auto-muting room sounds during nurse-patient communication; and auto-directing a healthcare workers electronic device to data associated with the patient in that room. In alternative embodiments, one or more of these additional functions are incorporated into a patient support apparatus.

20 Claims, 13 Drawing Sheets

Related U.S. Application Data

(60) Provisional application No. 62/600,000, filed on Dec. 18, 2017.

(51) Int. Cl.
| | |
|---|---|
| *A61G 12/00* | (2006.01) |
| *G16H 40/40* | (2018.01) |
| *H04B 5/00* | (2006.01) |
| *H04B 5/48* | (2024.01) |
| *H04B 5/70* | (2024.01) |
| *H04B 5/72* | (2024.01) |
| *H04L 67/12* | (2022.01) |
| *H04W 4/02* | (2018.01) |
| *H04W 88/08* | (2009.01) |
| *A61G 7/018* | (2006.01) |
| *G08B 5/22* | (2006.01) |

(52) U.S. Cl.
CPC .............. *H04L 67/12* (2013.01); *A61G 7/018* (2013.01); *A61G 2205/60* (2013.01); *G08B 5/222* (2013.01)

(58) Field of Classification Search
CPC ........ G08B 21/22; H04W 4/02; H04W 4/021; H04W 88/02; H04W 88/04; H04W 88/12
See application file for complete search history.

(56) References Cited

U.S. PATENT DOCUMENTS 11,110,020 B2 * 9/2021 Bodurka .................. H04L 67/12
2020/0121186 A1 * 4/2020 Collins, Jr. ............. H04L 67/10

* cited by examiner

SMART HOSPITAL HEADWALL SYSTEM

CROSS-REFERENCE TO RELATED APPLICATIONS

This application claims priority to U.S. patent application Ser. No. 16/217,203 filed Dec. 12, 2018, by inventor Alexander Bodurka and entitled SMART HOSPITAL HEADWALL SYSTEM, which in turn claims priority to U.S. provisional patent application Ser. No. 62/600,000 filed Dec. 18, 2017, by inventor Alexander Bodurka et al. and entitled SMART HOSPITAL HEADWALL SYSTEM, the complete disclosures of both of which are incorporated herein by reference.

BACKGROUND

The present disclosure relates to medical facilities having headwalls with one or more connectors that enable communication between a patient support apparatus (e.g. a bed, stretcher, cot, recliner, wheelchair, etc.) and one or more devices that are coupled to a headwall communication interface (e.g. a nurse call system, entertainment controls, room controls, etc.).

Medical facilities, such as hospitals, typically include a headwall having one or more outlets and/or other types of connectors into which the plugs of cables connected to medical devices can be inserted. For example, headwalls will typically include at least one outlet that interfaces with a nurse-call system and which is designed to accept a cable from a hospital bed, or from a hand-held pendant positioned on the bed. When the cable is plugged into this outlet, a patient positioned on the bed is able to press a button to summon a nurse and/or to communicate aurally with the nurse.

Existing headwall connectors also typically communicate with one or more environmental controls, such as one or more controls for in-room televisions, displays, and/or room lights. When the appropriate device and its associated cable are plugged into the headwall connector from a bed, pendant, or other device, a person is able to control the environmental control via the device (e.g. bed, pendant, or other device). Thus, for example, a patient positioned on a bed is able to control the volume of a television in the room via controls on the bed due to a cable being connected from the bed to the headwall. In some instances, a single cable is plugged into a single connector on the headwall and used for communicating both with the nurse call system of the medical facility, and for communicating with the one or more environmental controls. In such instances, the headwall connector is coupled to a room interface board that forwards the environmental control signals to the appropriate environmental control unit, and forwards the nurse call signals to the appropriate component of the nurse call system.

SUMMARY

A headwall unit mounted to a fixed location within a healthcare facility room is provided that enables aural communications between a patient positioned on a patient support apparatus in that room and a healthcare worker positioned remotely, such as at a nurses' station. In addition to this functionality, the headwall unit provides additional functionality, including, but not limited to, one or more of the following: determining when a healthcare worker enters/exits the room; determining when the patient support apparatus exits/enters the room; storing/retrieving medical device data associated with a patient; directing medical device data to one or more displays in the room; auto-updating, auto-retrieving, and/or auto-displaying medical device data upon healthcare worker entry into the room; auto-muting room sounds during nurse-patient communication; automatically shutting down electronic devices (e.g. a television) when a patient support apparatus is moved out of a room; and automatically directing a healthcare worker's electronic device to data associated with the patient in that room. In other embodiments, any one or more of these additional functions is incorporated into a patient support apparatus.

According to one embodiment of the present disclosure, a stationary communication unit is provided that is adapted to be mounted in a room of a healthcare facility. The stationary communication unit includes a first transceiver, a second transceiver, and a controller. The first transceiver communicates with a patient support apparatus and receives requests to communicate with a caregiver when the caregiver is remotely located. The requests are initiated by a patient supported on the patient support apparatus. The second transceiver communicates with a nurse call system port installed on a wall of the room, such as a headwall. The controller forwards the request to the nurse call system port via the second transceiver. The controller is also adapted to receive data from a non-patient support apparatus medical device positioned in the room and to store the data for retrieval by authorized individuals.

According to other aspects of the present disclosure, the stationary communication unit may further include a third transceiver adapted to directly receive the data from the medical device positioned in the room. Additionally, or alternatively, the first transceiver may receive the data from the medical device and may do so in either or both of the following manners: (1) directly from medical device; and (2) directly from the patient support apparatus which, in turn, receives the data from the medical device via a transceiver positioned on the patient support apparatus.

In some embodiments, the second transceiver is a wired transceiver and the nurse call system port is a multi-pin receptacle adapted to receive a cable having a multi-pin connector.

The data may be stored locally at the stationary communication unit, or it may be stored at a remote server. When stored remotely, the stationary communication unit may include a network transceiver adapted to forward the data to a healthcare facility network via the network transceiver.

The stationary communication unit, in some embodiments, is further adapted to receive a request for the data from a requesting device positioned in the room and to transmit the data to the requesting device in response thereto.

The stationary communication unit also includes, in some embodiments, a patient support apparatus presence detection subsystem. The patient support apparatus presence detection subsystem detects when the patient support apparatus is present in the room and when the patient support apparatus is not present in the room. The patient support apparatus presence detection subsystem may include an infrared transceiver adapted to communicate with the patient support apparatus when the patient support apparatus is positioned within range of the infrared transceiver.

In some of the embodiments in which the stationary communication unit includes a patient support apparatus presence detection subsystem, the controller of the stationary communication unit is further adapted to communicate with an entertainment device positioned in the room. The controller automatically sends a command to the entertainment device in response to detecting that the patient support apparatus is not present in the room, and the command instructs the entertainment device to do at least one of the following: (1) turn off, and (2) reduce a volume of sound emitted from the entertainment device.

The stationary communication unit may also or alternatively include a caregiver presence detection subsystem that detects when the caregiver is present in the room and when the caregiver is not present in the room. In some embodiments, the caregiver presence detection subsystem detects a presence of the caregiver by communicating with a mobile device carried by the caregiver. The mobile device includes a unique identifier and a wireless transceiver adapted to communicate the unique identifier to the controller when the mobile device is positioned within the room.

In some embodiments, the controller is further adapted to transmit a uniform resource locator (URL) to a mobile device carried by the caregiver when the caregiver is in the room. The URL identifies a location where the data is stored, or a web page where the resources enabling the mobile electronic device to access the data are stored. In some embodiments, the URL identifies a location accessible to the mobile device using conventional web browsing software installed on the mobile device, thereby relieving the caregiver of the task of having to install special software on his or her mobile device in order to retrieve the data. The data may include data from multiple medical devices.

The controller communicates with an entertainment device positioned in the room in some embodiments. In such embodiments, the controller is adapted to automatically send a volume change command to the entertainment device in response to the request to communicate with the caregiver.

The controller may also be adapted to receive caregiver audio signals from the nurse call system port and forward the caregiver audio signals to the patient support apparatus using the first transceiver. In such embodiments, the controller is further adapted to receive patient audio signals from the patient support apparatus and forward the patient audio signals to the nurse call system port using the second transceiver.

According to another embodiment of the present disclosure, a stationary communication unit adapted to be mounted in a room of a healthcare facility is provided. The stationary communication unit includes a first transceiver and a controller. The first transceiver is adapted to communicate with a mobile device carried by a caregiver when the caregiver is in the room. The controller sends a uniform resource locator (URL) to a mobile device carried by the caregiver when the caregiver is in the room. The URL identifies a location where data regarding a medical device used with a patient associated with the room is stored.

In some embodiments, the stationary communication unit further includes a second transceiver. The first transceiver communicates with a patient support apparatus positioned in the room and receives a patient-initiated request to communicate with a caregiver when the caregiver is remotely located. The second transceiver communicates with a nurse call system port mounted to a wall of a room. The controller forwards the request to the nurse call system port via the second transceiver.

The URL may identify a remote server. In some embodiments, the URL is unique for the room and/or the bay in which the stationary communication unit is mounted.

In some embodiments, the first transceiver receives the data regarding the medical device from a medical device positioned in the room and the controller is adapted to forward the received data to the location identified by the URL.

In some embodiments, the medical device is a patient support apparatus or another medical device used in the treatment of the patient.

According to at least one aspect of the present disclosure, the first transceiver receives patient support apparatus data from the patient support apparatus and the controller forwards the received patient support apparatus data to the location identified by the URL. Both the patient support apparatus data and the data regarding the medical device may be transmitted by the patient support apparatus to the first transceiver of the stationary communication unit.

According to another aspect of the present disclosure, a stationary communication unit is provided that is adapted to be mounted in a room of a healthcare facility. The stationary communication unit includes a first transceiver, a second transceiver, a caregiver presence detection subsystem, and a controller. The first transceiver communicates with a patient support apparatus and receives a patient-initiated request to communicate with a caregiver when the caregiver is remotely located, the request being initiated by a patient supported on the patient support apparatus. The second transceiver communicates with a nurse call system port mounted to a wall of a room in which the stationary communication unit is mounted. The caregiver presence detection subsystem detects when the caregiver is present in the room and when the caregiver is not present in the room. The controller forwards the request to the nurse call system port via the second transceiver and is adapted to automatically send data to a display positioned in the room in response to detecting a presence of the caregiver in the room.

According to other aspects of the present disclosure, the display is positioned on the patient support apparatus, on a mobile device carried by a caregiver, or is mounted to a wall or ceiling of the room.

In some embodiments, the data is received by the controller via the first transceiver, and the data comes from multiple medical devices positioned in the room.

The caregiver presence detection subsystem may be adapted to detect the caregiver's presence/absence by communicating with a mobile device carried by the caregiver. The mobile device includes a unique identifier and a transceiver adapted to communicate the unique identifier to the controller when the mobile device is positioned within the room.

The controller may further be adapted to transmit a uniform resource locator (URL) to the mobile device when the caregiver is in the room. The URL identifies a location where the data is stored that is accessible to the mobile device using conventional web browsing software installed on the mobile device such that the additional data may be displayed on the display. Alternatively, the URL identifies a location where a web page provides the mobile electronic device with a tool for accessing, displaying, storing, and/or formatting the data. In some embodiments, the tool utilizes a conventional web browser on the mobile electronic device such that no additional software needs to be installed on the mobile electronic device in order to enable the device to access, display, store, and/or format the data.

In some embodiments, the data comes from a medical device positioned in the room and the controller is adapted to receive updated data from the medical device while the caregiver is in the room. The controller sends the updated data to the display while the caregiver is in the room.

According to another embodiment of the present disclosure, a patient support apparatus is provided that includes a support surface, a sensor, a transceiver, and a controller. The support surface is adapted to support a patient thereon. The sensor senses a parameter of the patient support apparatus. The transceiver communicates with a mobile device carried by a caregiver when the caregiving is positioned within a vicinity of the patient support apparatus. The controller sends a uniform resource locator (URL) to the mobile device when the caregiver is in the vicinity of the patient support apparatus and the URL identifies a location where the parameter is stored.

In some embodiments, the URL identifies a location unique to the patient support apparatus.

The patient support apparatus may further be adapted to receive data from a medical device used with the patient and to forward the data to the location identified by the URL.

In at least one embodiment, the URL sent by the patient support apparatus identifies a location accessible to the mobile device using conventional web browsing software installed on the mobile device.

The patient support apparatus may further include a caregiver presence detection subsystem adapted to detect when the caregiver is present in the vicinity of the patient support apparatus and when the caregiver is not in the vicinity of the patient support apparatus.

The patient support apparatus, in some embodiments, further comprises a base having a plurality of wheels; a frame on which the support surface is supported; a lift subsystem for raising and lowering the frame with respect to the base; a plurality of siderails adjacent the support surface that are movable between raised and lowered positions; and a scale subsystem adapted to detect weight applied by the patient to the support surface.

In some embodiments, the sensor is a component of the scale subsystem.

The patient support apparatus may further include a second transceiver adapted to forward the parameter to the location identified by the URL.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration is used in the description herein of various embodiments (e.g. first, second, third, etc.). Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
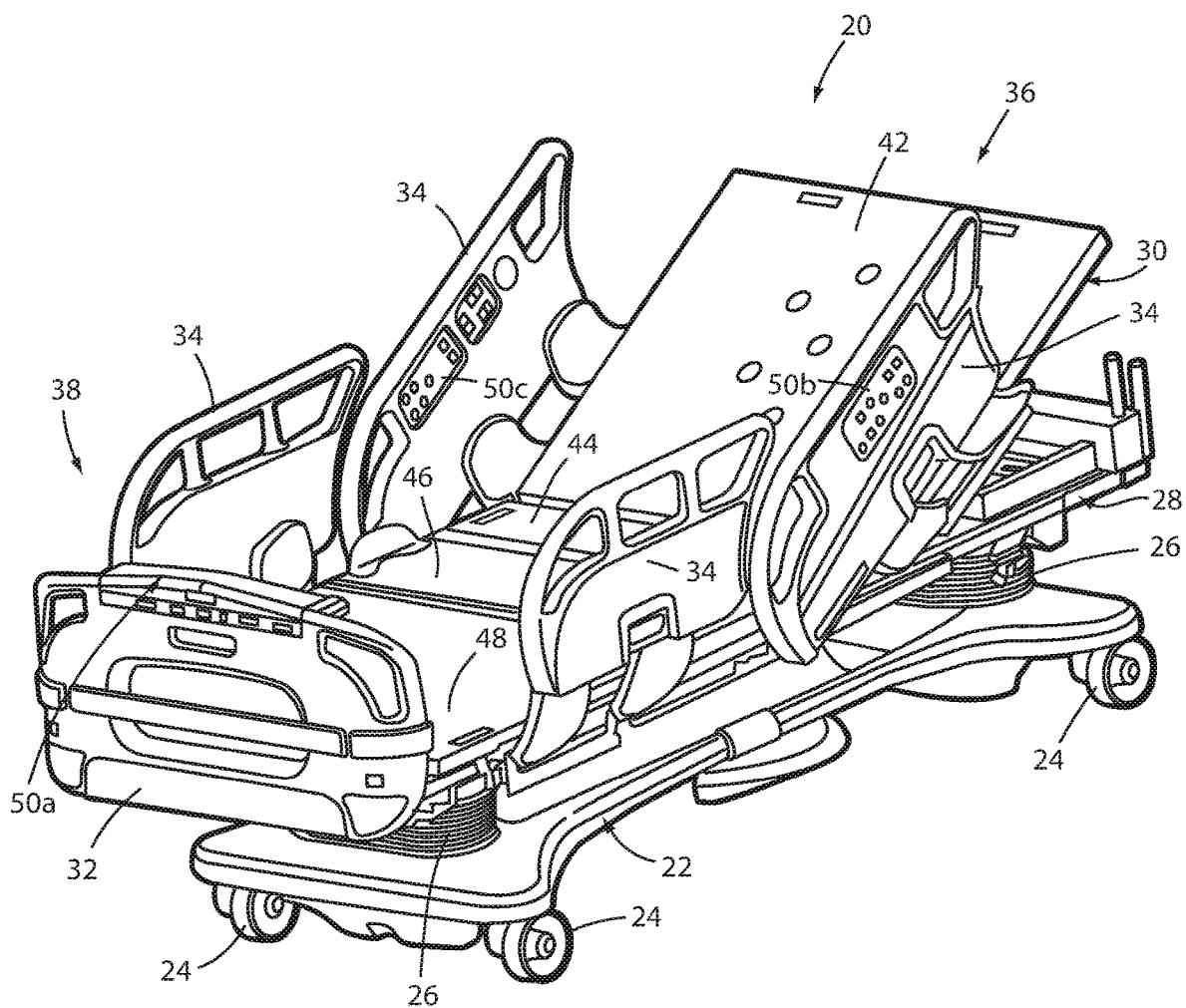
FIG. 1 is a perspective view of a patient support apparatus according to a first embodiment of the disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a wheelchair, or any other mobile structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 32 (which may be removable) and a plurality of siderails 34. Siderails 34 are all shown in a raised position in FIG. 1 but are each individually movable to a lower position in which ingress into, and egress out of, patient support apparatus 20 is not obstructed by the lowered siderails 34.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. Patient support apparatus 20 is designed so that when a person lies thereon, his or her head will be positioned adjacent head end 36 and his or her feet will be positioned adjacent foot end 38.

Litter frame 28 provides a structure for supporting support deck 30, footboard 32, and siderails 34. Support deck 30 provides a support surface for a mattress 40 (FIG. 2), such as, but not limited to, an air, fluid, or gel mattress. Alternatively, another type of soft cushion may be supported on support deck 30 so that a person may comfortably lie and/or sit thereon. The top surface of the mattress or other cushion forms a support surface for the patient. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Patient support apparatus 20 further includes a plurality of user interfaces 50 that enable a user of patient support apparatus 20, such as a patient and/or an associated caregiver, to control one or more aspects of patient support apparatus 20. In the embodiment shown in FIG. 1, patient support apparatus 20 includes a footboard user interface 50a, a pair of outer siderail user interfaces 50b (only one of which is visible), and a pair of inner siderail user interfaces 50c (only one of which is visible). Footboard user interface 50a and outer siderail user interfaces 50b are intended to be used by caregivers, or other authorized personnel, while inner siderail user interfaces 50c are intended to be used by the patient associated with patient support apparatus 20. Not all of the user interfaces 50 include the same controls and/or functionality. In the illustrated embodiment, footboard user interface 50a includes a substantially complete set of controls for controlling patient support apparatus 20 while user interfaces 50b and 50c include a selected subset of those controls.

The controls of user interfaces 50 allow a user to control one or more of the following: change a height of support deck 30, raise or lower head section 42, activate and deactivate a brake for wheels 24, arm and disarm an exit detection system and, as will be explained in greater detail below, communicate with the particular IT infrastructure installed in the healthcare facility in which patient support apparatus 20 is positioned. Inner siderail user interfaces 50c may also include a nurse call control that enables a patient to call a nurse. A speaker and microphone are included in order to allow the patient to aurally communicate with the remotely positioned nurse.

Footboard user interface 50a is implemented in the embodiment shown in FIG. 1 as a control panel having a lid (flipped down in FIG. 1) underneath which is positioned a plurality of controls. The controls may be implemented as buttons, dials, switches, or other devices. Any of user interfaces 50a-c may also include a display for displaying information regarding patient support apparatus 20. The display may be a touchscreen in some embodiments.

The mechanical construction of patient support apparatus 20, as shown in FIG. 1, is the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. The construction of patient support apparatus 20 may take on a wide variety of different forms. In some embodiments, other than the components described below, patient support apparatus 20 is constructed in any of the manners described in commonly assigned, U.S. Pat. No. 8,689,376 issued Apr. 8, 2014 by inventors David Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is hereby incorporated herein by reference. In other embodiments, those components of patient support apparatus 20 not described below are constructed in any of the manners described in commonly assigned, U.S. patent application Ser. No. 13/775,285 filed Feb. 25, 2013 by inventors Guy Lemire et al. and entitled HOSPITAL BED, the complete disclosure of which is also hereby incorporated herein by reference. In still other embodiments, those components of patient support apparatus 20 not described below are constructed in any of the manners disclosed in commonly assigned, U.S. patent application Ser. No. 14/212,009 filed Mar. 14, 2014 by inventors Christopher Hough et al., and entitled MEDICAL SUPPORT APPARATUS. The mechanical construction of patient support apparatus 20 may also take on forms different from what is disclosed in the aforementioned references.

Figure 2:
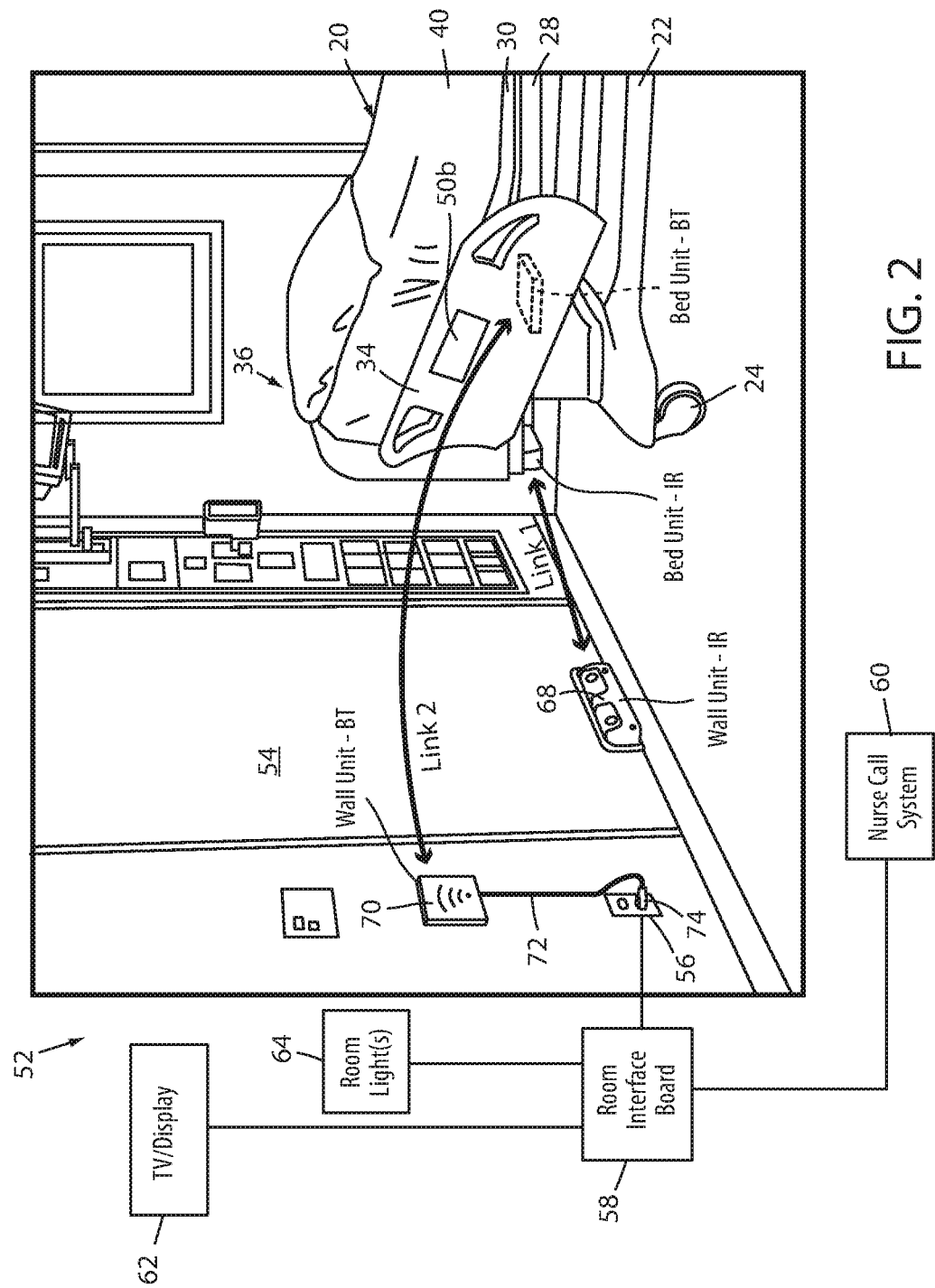
FIG. 2 is a perspective view of the patient support apparatus of FIG. 1 shown in a hospital room adjacent a headwall unit comprised of separate first and second wall units.

FIG. 2 illustrates patient support apparatus 20 coupled to the IT infrastructure 52 of an illustrative healthcare facility according to one common configuration. As shown therein, the healthcare facility includes a headwall 54, a cable port 56 mounted to the headwall 54, a room interface board 58 in communication with cable port 56, and a plurality devices and components in communication with the room interface board 58, such as a nurse call system 60, a TV and/or display 62, and one or more room lights 64. Cable port 56, room interface board 58, nurse call system 60, TV/display 62, and room lights 64 may all be conventional pre-existing components that are installed in the healthcare facility independently of patient support apparatus 20 and its associated headwall units 66, as will be discussed in more detail below. Additional IT infrastructure beyond what is shown in FIG. 2 may also be present in the healthcare facility, some examples of which are discussed in more detail below with respect to FIGS. 4 & 5.

TV/display 62 is a conventional television, computer display, monitor, or the like that includes a display screen on which images are able to be displayed. Room lights 64 provide lighting to one or more sections of the room in which patient support apparatus 20 is located. Room lights 64 may be conventional overhead lights and/or one or more night lights or other more localized lights within the room. Nurse call system 60 may be a conventional nurse call system having one or more nurses' stations positioned throughout the healthcare facility. Nurse call system 60 routes patient calls from patient support apparatus 20 to one or more nurses' stations so that the patient is able to speak with a remotely positioned nurse at a nurses' station while the patient is supported on patient support apparatus 20, as is known in the art.

Figure 4:
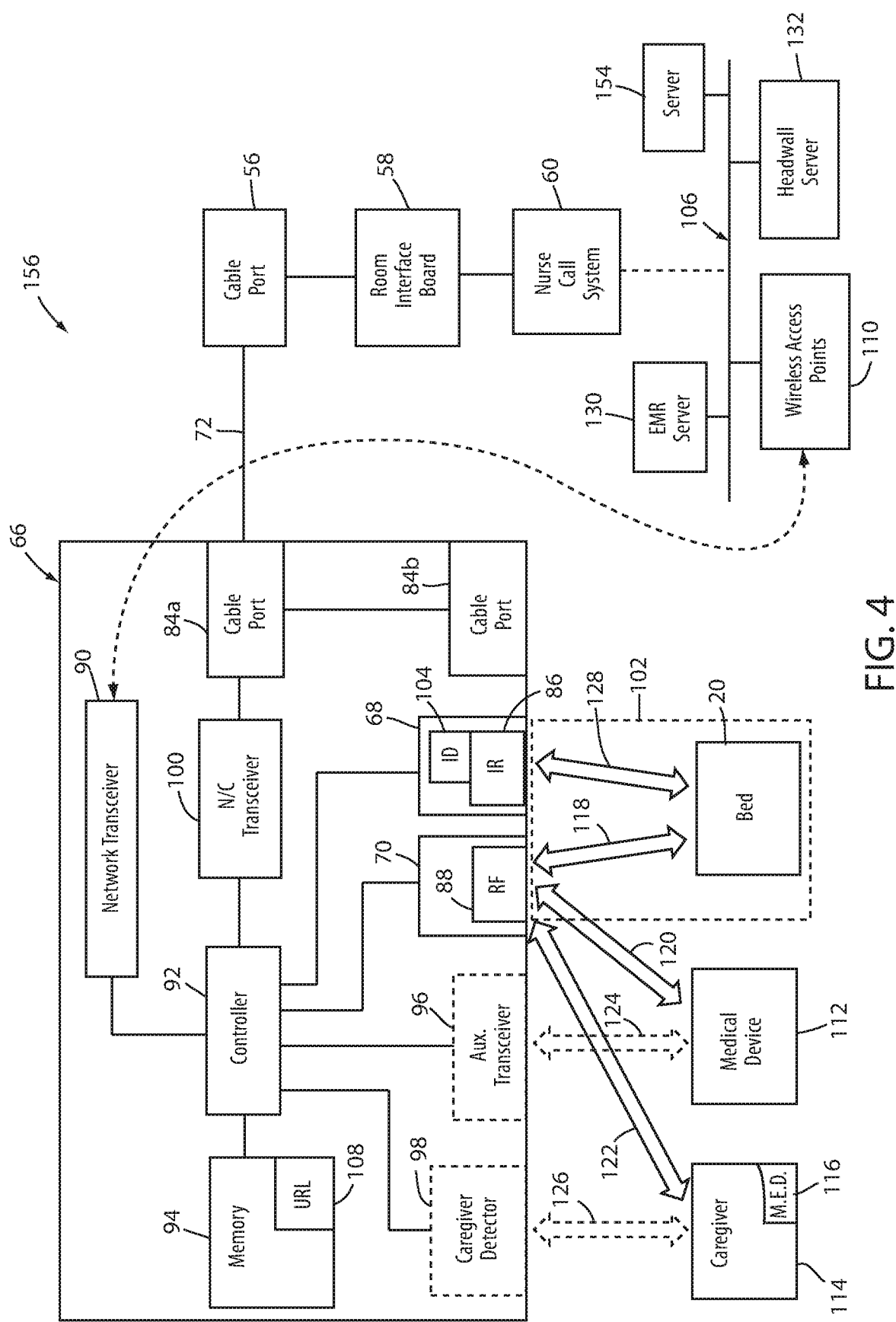
FIG. 4 is a block diagram one embodiment of a headwall system incorporating the headwall unit of FIG. 2.

Patient support apparatus 20 is adapted to wirelessly communicate with a first wall unit 68 and a second wall unit 70. First and second wall units 68 and 70 together form a headwall unit 66. In the embodiment shown in FIG. 1, first and second wall units 68 and 70 are two separate wall units. In other embodiments, such as shown in FIG. 4, wall units 68 and 70 are combined into a single wall unit having a single housing, as discussed in more detail below. Regardless of whether coupled together in a single housing or separated into two physically disparate units, first and second wall units 68 and 70 are adapted to communicate with each other, in at least some embodiments. Such communication takes place via a wired connection when units 68 and 70 are combined in a single housing, and may take place wirelessly when units 68 and 70 are physically separated. In still other embodiments, units 68 and 70 are not adapted to communicate with each other.

Second wall unit 70 includes a cable 72 that is coupled to cable port 56 (FIG. 2). Cable 72 allows second wall unit 70 to communicate with cable port 56 and all of the components in communication with cable port 56 (e.g. nurse call system 60, room interface board 58, etc.). Cable 72 includes a connector 74 that is adapted to mate with cable port 56. Connector 74 may vary from room to room and from healthcare facility to healthcare facility depending upon the particular type of cable port 56 that is installed within a particular room of a particular healthcare facility.

Figure 3:
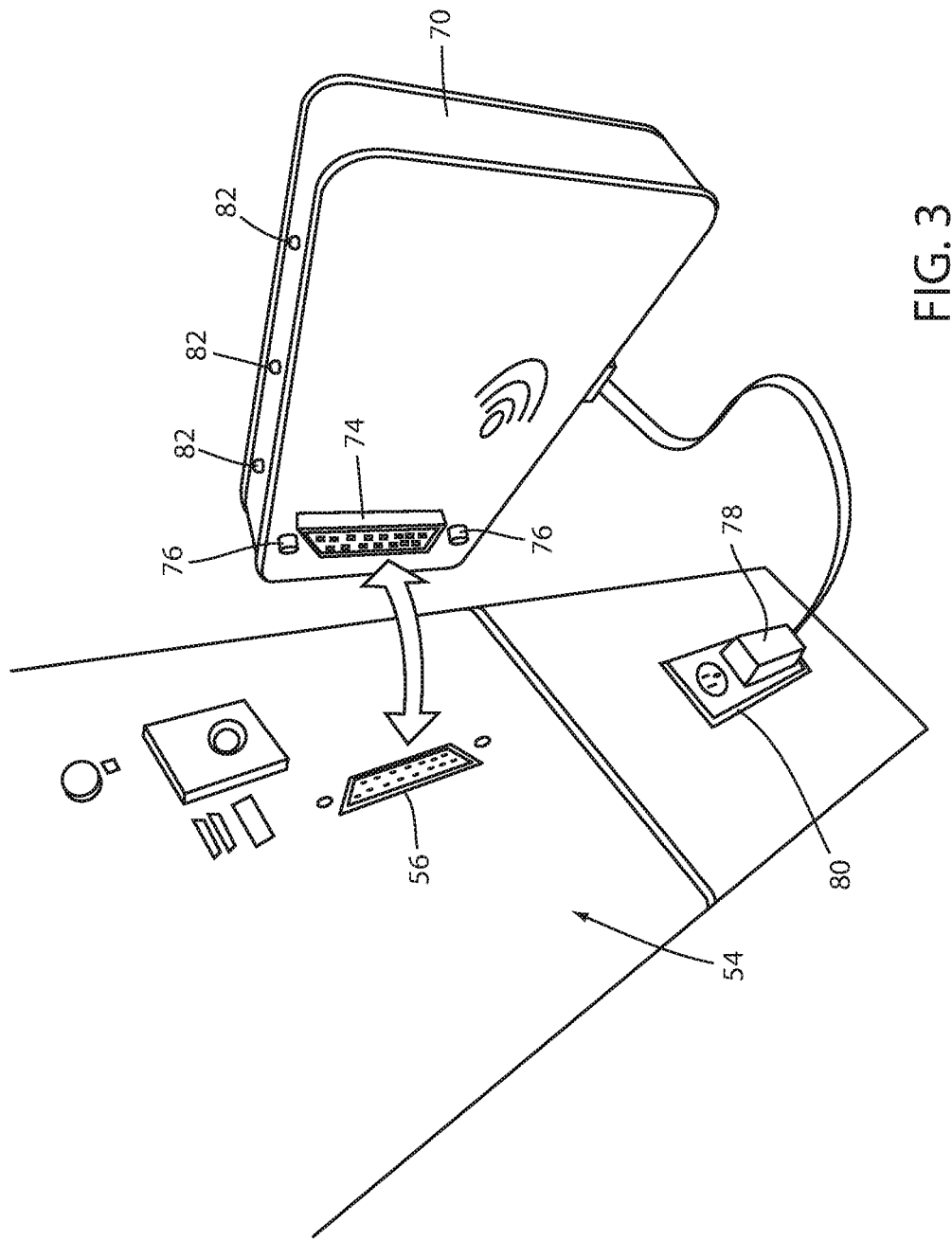
FIG. 3 is perspective view of an alternative embodiment of the second wall unit of FIG. 2.

FIG. 3 illustrates an alternative embodiment of second wall unit 70 in which cable 72 has been omitted. In this embodiment, second wall unit 70 has connector 74 integrated therein and second wall unit 70 couples directly to cable port 56. Connector 74 is adapted to be inserted into cable port 56, which is a conventional cable interface that exists within a medical facility. Cable port 56 is a receptacle that is dimensioned and shaped to selectively frictionally retain connector 74 therein and to support the entire second wall unit 70. One or more alignment posts 76 may be included with connector 74 in order to more securely retain second wall unit 70 to cable port 56, if desired.

In the embodiment shown in FIG. 3, connector 74 is a 37 pin connector that includes 37 pins adapted to be inserted into 37 mating sockets of cable port 56. Such 37 pin connections are one of the most common types of connectors found on existing headwalls of medical facilities for making connections to the nurse call system 60 and/or the room interface board 58. Connectors 74 of FIGS. 2 and 3 are therefore configured to mate with one of the most common type of cable ports 56 used in medical facilities. Such 37 pin connectors, however, are not the only type of connectors, and it will be understood that second wall unit 70 can utilize different types of connectors 74 (whether integrated therein or attached to cable 72) that are adapted to electrically couple to different types of cable ports 56. One example of such an alternative cable port 56 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of cable ports 56 and corresponding cable connectors 74 may be utilized.

In the embodiment shown in FIG. 3, second wall unit 70 includes an electrical plug 78 adapted to be inserted into a conventional electrical outlet 80. Electrical plug 78 enables second wall unit 70 to receive power from the mains electrical supply via outlet 80. It will be appreciated that, in some embodiments, second wall unit 70 is battery operated and plug 78 may be omitted. In still other embodiments, second wall unit 70 may be both battery operated and include plug 78 so that, in the event of a power failure, battery power supplies power to second wall unit 70, and/or in the event of a battery failure, electrical power is received through outlet 80.

The embodiment of second wall unit 70 shown in FIG. 3 also includes a plurality of status lights 82. Status lights 82 provide visual indications about one or more aspects of second wall unit 70. For example, in some embodiments, the illumination of one of status lights 82 indicates that second wall unit 70 is in successful communication with room interface board 58 and/or patient support apparatus 20. The illumination of one or more additional status lights 82 may also or alternatively indicate that power is being supplied to second wall unit 70 and/or the status of a battery included within second wall unit 70. In addition, the illumination of another one of status lights 82 may indicate that second wall unit 70 is in successful communication with a mobile electronic device carried by a caregiver, such as, but not limited to, a smart phone, as will be discussed in greater detail below. A status light 82 may also be illuminated by the circuitry within second wall unit 70 in those situations where second wall unit 70 detects the presence of a caregiver and/or patient support apparatus 20, as will also be discussed in greater detail below.

Headwall unit 66 (FIG. 4) is adapted to wirelessly receive signals from patient support apparatus 20 and deliver the signals to cable port 56 in a manner that matches the way the signals would otherwise be delivered to cable port 56 if a conventional nurse call cable were connected between patient support apparatus 20 and cable port 56. In other words, patient support apparatus 20 and headwall unit 66 cooperate to provide signals to cable port 56 in a manner that is transparent to cable port 56 and room interface board 58 such that these components cannot detect whether they are in communication with patient support apparatus 20 via wired or wireless communication. In this manner, a healthcare facility can utilize the wireless communication abilities of one or more patient support apparatuses 20 without having to make any changes to their existing cable ports 56 (or to their nurse call system 60 or room interface boards 58).

In addition to sending signals received from patient support apparatus 20 to cable port 56, headwall unit 66 is also adapted to forward signals received from cable port 56 to patient support apparatus 20. Headwall unit 66 is therefore adapted to provide bidirectional communication between patient support apparatus 20 and cable port 56. Such bidirectional communication includes, but is not limited to, communicating audio signals between a person supported on patient support apparatus 20 and a caregiver positioned remotely from patient support apparatus 20 (which is accomplished by headwall unit 66 forwarding the audio signals of the person on patient support apparatus 20 to nurse call system 60, and vice versa).

Headwall unit 66 communicates the data and signals it receives from patient support apparatus 20 to room interface board 58 by directing the incoming data and signals it receives to the appropriate pin or pins of cable port 56. For example, when cable port 56 includes 37 sockets for coupling to a 37 pin plug, it is common for pins #30 and #31 to be used for indicating a "priority alert," which is often synonymous with an alert that is issued when a patient exits from patient support apparatus 20. Further, depending upon the particular configuration that has been implemented at a particular healthcare facility, the connection between pins #30 and #31 may be normally open or it may be normally closed. Regardless of whether it is normally open or normally closed, whenever headwall unit 66 receives a message from patient support apparatus 20 that a person has exited from patient support apparatus 20, headwall unit 66 utilizes a nurse call transceiver 100 (discussed in more below) to change the status of pins #30 and #31 such that they switch from whatever state they are normally in to their opposite state. Headwall unit 66 therefore reacts to the exit message it receives from patient support apparatus 20 by either opening or closing pins #30 and #31. The nurse call system 60 that is communicatively coupled to cable port 56 interprets this opening or closing of pins #30 and #31 in the same manner as if a cable were coupled between cable port 56, such as by sending the appropriate signals to one or more nurse's stations, flashing a light outside the room of patient support apparatus 20, forwarding a call to a mobile communication device carried by the caregiver assigned to the patient of patient support apparatus 20, and/or taking other steps, depending upon the specific configuration of the nurse call system.

In addition to sending data indicating that a patient of patient support apparatus 20 has exited, or is about to exit, therefrom, patient support apparatus 20 is configured, in at least one embodiment, to wirelessly send to headwall unit 66 at least the following additional messages: messages to turn on or off one or more room lights; messages to turn on or off one or more reading lights; messages to increase or decrease the volume of a nearby television set or radio; messages to change a channel of the nearby television set or radio; and messages containing audio packets generated from one or more microphones on the patient support apparatus 20 into which the patient of patient support apparatus 20 speaks when desiring to communicate with a remote caregiver.

In other embodiments, patient support apparatus 20 is configured to wirelessly send to headwall unit 66 any one or more of the following messages, either in addition to or in lieu of any one or more of the messages just mentioned: messages indicating the current status of one or more siderails 34 of patient support apparatus 20 (e.g. whether the side rails are up or down, or have changed position); messages indicating the current status of a brake on patient support apparatus 20; messages indicating the current status of the height of support deck 30 relative to base 22 (e.g. such as whether support deck 30 is at its lowest height or not); messages indicating the current angle of head section 42; messages indicating the current status of an exit detection system (e.g. whether the exit detection system is armed or not); messages indicating the current charging status of one or more batteries on patient support apparatus 20; messages indicating the current status of an alternating current (A/C) power cable on patient support apparatus 20 (e.g. whether it is plugged in or not); diagnostic information about patient support apparatus 20; messages containing patient data gathered from one or more sensors on board patient support apparatus 20; message containing patient data gathered from one or more medical devices that are separate from patient support apparatus 20 but which communicate such data to patient support apparatus 20; and/or any other messages containing information about patient support apparatus 20, the patient supported thereon, and/or a caregiver associated with the patient.

In at least one embodiment, headwall unit 66 is further configured to transmit information to cable port 56 that does not originate from patient support apparatus 20, but instead is generated internally within headwall unit 66. For example, in one embodiment, headwall unit 66 is adapted to forward to cable port 56 a signal that indicates a "cord-out" alert whenever the communication link between headwall unit 66 and patient support apparatus 20 is unintentionally lost. In many instances, when a conventional cable is coupled between cable port 56 and a hospital bed, and the cable is inadvertently disconnected, the electrical status of pins 10 and 11 (in a conventional 37 pin connection) will be changed such that the nurse call system will recognize that the cable has become disconnected, and will therefore issue an appropriate alert to the appropriate personnel. Headwall unit 66 is configured to make the same changes to pins 10 and 11 when it unintentionally loses communication with patient support apparatus 20 that would be made to pins 10 and 11 if a cable connection between patient support apparatus 20 and cable port 56 were to become unintentionally disconnected. Thus, headwall unit 66 and patient support apparatus 20 together include the same ability to provide an indication to cable port 56 of an unintentional disconnection that exists in some currently-available cable connections to cable interfaces. Still other types of signals that originate from within headwall unit 66 may also be sent to cable port 56 in addition to, or in lieu of, this cord-out alert.

In addition to forwarding any of the above-described messages or signals to cable port 56, headwall unit 66 is also adapted, in at least one embodiment, to forward the following messages to patient support apparatus 20 based on information it receives from devices in communication with cable port 56: messages indicating the establishment and disestablishment of a nurse-call communication link (e.g. messages used for turning on and off a "nurse answer" light on patient support apparatus 20); and messages containing audio packets of a caregiver's voice (generated from a microphone into which the caregiver speaks and forwarded to the appropriate pins of cable port 56).

In other embodiments, one or more additional messages are also transmitted to patient support apparatus 20 that originate from within, rather than from any of the devices in communication with cable port 56. Such messages include any one or more of the following: the charge status of a battery within or a battery inside first wall unit 68; acknowledgements of messages transmitted from patient support apparatus 20 to; messages used to establish, maintain, and disestablish the communication link between and one or more of the following: patient support apparatus 20, a mobile electronic device associated with a caregiver, and/or one or more medical devices associated with the patient; and messages containing patient data and/or medical device data that is stored within and/or headwall unit 66. Still other messages communicated to and/or from headwall unit 66 will be discussed in greater detail below.

As was noted previously, first wall unit 68 and second wall unit 70 may be integrated into a single housing, in some embodiments. FIG. 4 illustrates one such embodiment. FIG. 4 illustrates a headwall system 156 in which headwall unit 66 includes both first wall unit 68 and second wall unit 70, as well as other components that will be described in more detail below. In some embodiments, headwall unit 66 includes first and second cable ports 84a and 84b. First cable port 84a is adapted to receive one end of cable 72. The other end of cable 72, as noted, plugs into cable port 56. Second cable port 84b is adapted to receive a nurse call cable from patient support apparatus 20 when patient support apparatus 20 is intended to communicate with the room interface board 58 via a wired connection instead of a wireless connection. In those embodiments of headwall unit 66 where first wall unit 68 and second wall unit 70 are physically separated, cable port 84a is built into second wall unit 70.

In those situations where it is desired to have patient support apparatus 20 communicate with room interface board 58 via wires, rather than wirelessly, a nurse call cable from patient support apparatus 20 plugs into second cable port 84b and cable 72 is plugged into first cable port 84a and cable port 56 of headwall 54. In this arrangement, headwall unit 66 acts as a pass-through unit with respect to the signals on the nurse call cable. That is, data communicated to headwall unit 66 via second cable port 84b is transferred directly to first cable port 84a, and data communicated to headwall unit 66 via first cable port 84a is transferred directly to second cable port 84b.

In some alternative embodiments, headwall unit 66 is implemented as a device completely separate from the communication channel between patient support apparatus 20 and room interface board 58. In such embodiments, a cable from patient support apparatus 20 may be plugged directly into cable port 56 via a cable, or patient support apparatus 20 may communicate with port 56 wirelessly via a circuitry that is separate from headwall unit 66. Thus, in some embodiments, headwall unit 66 may be modified to provide functionality entirely separate from conventional nurse call functionality. In such embodiments, the nurse call functionality is handled by one or more conventional components that are not shown in the drawings. For purposes of the written description herein, however, headwall unit 66 will be described as carrying out both the function of coupling patient support apparatus 20 to the nurse call system, as well as the additional functionality described in greater detail below.

As is also shown in FIG. 4, headwall unit 66 includes a first wireless transceiver 86, a second wireless transceiver 88, a network transceiver 90, a controller 92, a memory 94, an auxiliary transceiver 96, a caregiver detector 98, and a nurse call transceiver 100. First transceiver 86 is adapted to communicate with a patient support apparatus 20 positioned within a bay area 102 and second transceiver 88 is adapted to communicate with patient support apparatus 20 and other devices that are positioned in the room in which headwall unit 66 is located. Controller 92 is a conventional microcontroller, in at least one embodiment. For example, in one embodiment, controller 92 is any one of the i.MX family of system-on-chip (SoC) processors and/or any one of the Kinetis K60 family of microcontroller units (MCUs), both of which are marketed by Freescale Semiconductor of Austin, Texas. Other microcontroller units, however, may be used. In general, controller 92 includes any and all electrical circuitry and components necessary to carry out the functions and algorithms described herein, as would be known to one of ordinary skill in the art. Such circuitry may include one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions within headwall unit 66, or they may reside in a common location within headwall unit 66. When physically distributed, the components may communicate using any suitable serial or parallel communication protocol, such as, but not limited to, CAN, LIN, Firewire, I-squared-C, RS-232, RS-465, universal serial bus (USB), etc. The instructions followed by controller 92 in carrying out the functions described herein, as well as the data necessary for carrying out these functions, are stored in one or more accessible memories, such as, but not limited to, memory 94.

Memory 94 (FIG. 4), in addition to storing instructions followed by controller 92, stores data received from patient support apparatus 20 and/or from other devices positioned within the room in which headwall unit 66 is positioned. As will be discussed in greater detail below, such data may include patient data, sensor data, device data, alerts, communication preferences, and other data. As will also be explained in greater detail, memory 94 contains a Uniform Resource Locator (URL) 108 that controller 92 transmits to mobile electronic devices 116, such as a smart phones, carried by caregivers and/or other authorized individuals associated with the healthcare facility. The URL enables the mobile electronic device 116 to easily access and retrieve data stored in memory 94 (or elsewhere) that relates to patient, patient support apparatus 20, and/or other medical devices 112 associated with headwall unit 66.

Network transceiver 90 (FIG. 4) is adapted to communicate with one or more wireless access points 110 of healthcare facility network 106. In some embodiments, network transceiver 90 is a WiFi transceiver (IEEE 802.11) adapted to communicate with access points 110 using any of the various WiFi protocols (IEEE 802.11b, 801.11g, 802.11n, 802.11ac . . . , etc.). In still other embodiments, network transceiver 90 is adapted to communicate using any of the frequencies, protocols, and/or standards disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference. In still other embodiments, network transceiver 90 may take on other forms and/or protocols.

Nurse call transceiver 100 (FIG. 4) is adapted to communicate with cable port 84a and the cable 72 coupled thereto. Nurse call transceiver 100 therefore converts messages from controller 92 into the proper form to match the communication characteristics of cable port 56. In this regard, nurse call transceiver 100 selects which pin of the multiple pins certain data is to be communicated over and/or converts the data into the proper format and/or protocol for communicating with room interface board 58 and the devices in communication with room interface board 58.

Auxiliary transceiver 96 (FIG. 4) is a transceiver that is included in some embodiments of headwall unit 66. When included, auxiliary transceiver 96 is adapted to communicate with one or more non-patient support apparatus medical devices 112 positioned within the room. When included, auxiliary transceiver 96 uses a different communication protocol than first and second transceivers that matches the communication protocol of one or more medical devices 112. In some embodiments auxiliary transceiver 96 utilizes the ZigBee communications protocol (IEEE 802.15.4). In other embodiments, a different standard is used. Still further, as noted, in some embodiments of headwall unit 66, auxiliary transceiver 96 is omitted. In such embodiments, second transceiver 88 is used to communicate with one or more medical devices 112.

Caregiver detector 98 (FIG. 4) is a device used to detect when a caregiver 114 associated with a patient or patient support apparatus 20 is positioned within the room and when such a caregiver is not positioned within the room. As with auxiliary transceiver 96, caregiver detector 98 may be omitted in some embodiments and its functionality carried out by second transceiver 88 and/or another transceiver. When caregiver detector 98 is included, it may take on a variety of different forms. In some embodiments, caregiver detector 98 comprises a conventional RF ID reader that wirelessly detects badges, or the like, worn by caregivers. Alternatively, caregiver detector 98 is a device that communicates with a conventional RF ID reader. In other embodiments, caregiver detector 98 is in communication with a conventional location and asset tracking system installed in the healthcare facility that keeps track of the location of caregivers. In another embodiment, caregiver detector 98 utilizes one or more cameras for detecting the presence/absence of caregivers. In at least one of these embodiments, caregiver detector 98 utilizes one or more of the caregiver detection principles disclosed in commonly assigned U.S. patent application Ser. No. 14/578,630 filed Dec. 22, 2014, by inventors Richard A. Derenne et al. and entitled VIDEO MONITORING SYSTEM, the complete disclosure of which is incorporated herein by reference. Other types of caregiver detection devices may alternatively, or additionally, be used.

In those embodiments where caregiver detector 98 is omitted, controller 92 may be configured to detect the presence/absence of a caregiver utilizing second transceiver 88. For example, each caregiver may be given a mobile electronic device 116, such as a smart phone or an ID card that broadcasts a unique identifier via the same communications protocol utilized by second transceiver 88. Second transceiver 88 listens for these broadcasts and uses the unique identifier to determine when a caregiver is positioned within range of headwall unit 66. As will be discussed in greater detail below, controller 92 is configured in some embodiments to take one or more automatic actions in response to detecting the entry or exit of a caregiver into the room. The automatic actions may depend upon the particular healthcare provider and/or the particular type of healthcare provider (e.g. the actions may differ for doctors, nurses, nurse assistants, technicians, administrative personnel, etc.).

Headwall unit 66 is typically positioned at the head of a bay area 102 (FIG. 4), which is the area where the patient support apparatus 20 typically remains when it is positioned within a particular room of the healthcare facility. In some healthcare facilities, one or more of the rooms are single patient support apparatus rooms in which only a single patient support apparatus is present (private rooms). In such rooms, there is only one bay 102. Healthcare facilities, however, typically include one or more rooms in which multiple patient support apparatuses 20 are positioned (semi-private rooms). In such rooms, there are multiple bays 102 for the multiple patient support apparatuses 20.

First wireless transceiver 86 of headwall unit 66 is part of first wall unit 68 and is adapted to communicate with patient support apparatus 20. In the illustrated embodiment, first transceiver 86 is implemented as an infrared transceiver and is adapted to communicate with patient support apparatus 20 only when patient support apparatus 20 is positioned within close proximity to headwall unit 66, such as when patient support apparatus 20 is positioned within the particular bay area 102 associated with that particular headwall unit 66. In other embodiments, it will be understood that first wireless transceiver 86 of headwall unit 66 may be implemented using short range communication media and/or protocols other than infrared communications, including, but not limited to, optical communications.

Each headwall unit 66 includes a unique identifier 104 that uniquely identifies that particular headwall unit 66 from the other headwall units 66 within the healthcare facility. This unique identifier is used by patient support apparatus 20 and/or other devices in communication with first transceiver 86 of headwall unit 66 to determine their location within a particular healthcare facility. When first transceiver 86 is able to communicate with patient support apparatus 20, controller 92 of headwall unit 66 transmits the unique identifier 104 to the patient support apparatus 20 (or other device). In the embodiment shown, unique identifier 104 is sent to patient support apparatus 20 only via first transceiver 86. It will be understood, however, that both first and second transceiver 86 and 88 may transmit identifier 104 to the patient support apparatus 20.

In order to determine location from the unique identifier, a controller on board patient support apparatus 20 (discussed more below) sends the unique identifier to one or more servers on a healthcare facility computer network 106, and the server converts the identifier into a location via a look-up table it has access to that correlates all of the headwall unit 66 identifiers within the healthcare facility to their respective locations. Alternatively, the controller on board patient support apparatus 20 consults an on-board look-up table that correlates the unique identifiers to locations within the healthcare facility and the controller determines the location of patient support apparatus 20 via the look-up table. In still another embodiment, unique identifier 104 identifies directly the room number in which headwall unit 66 is positioned, as well as the bay area 102 associated with headwall unit 66, and none of the receiving devices of the identifier (e.g. patient support apparatus 20) have to consult a look-up table to convert the ID 104 into a location, but instead are able to determine their location directly from the ID 104.

Second transceiver 88 of headwall unit 66 is adapted to communicate with patient support apparatus 20 using Radio Frequency (RF) communications that are not line-of-sight, unlike the IR communications of first transceiver 86. In some embodiments, second transceiver 88 is a Bluetooth transceiver configured to communicate using one or more of the Bluetooth standards (e.g. IEEE 802.14.1 or any of the standards developed by the Bluetooth Special Interest Group). It will be understood, however, that in other embodiments, second wireless transceiver 88 may utilize other forms of Radio Frequency (RF) and non-RF communication. For purposes of the following written description it will be assumed that second transceiver 88 communicates using conventional Bluetooth technology, although this written description is not meant to be an indication that other types of communication cannot be used between second transceiver 88 and the off-board devices with which it communicates, such as, but not limited to, patient support apparatus 20, one or more medical devices 112, and/or one or more mobile electronic devices 116 associated with caregivers 114.

In some embodiments, first transceiver 86 is used by headwall unit 66 to establish and periodically verify that patient support apparatus 20 (and/or other devices) are within bay area 102, while second transceiver 88 is used to communicate information back and forth between headwall unit 66 and patient support apparatus 20 (and other devices within the room). In such embodiments, first transceiver 86 may be used in situations where second transceiver is blocked or otherwise not functional. In still other modified embodiments, first transceiver 86 may be used to communicate data in addition to the location identifier 104, as well as to perform other functions besides establishing and verifying the presence of patient support apparatus 20 and/or other devices within bay area 102.

In addition to other communications, first and second transceivers 86 and 88 are utilized by controller 92 of headwall unit 66 to communicate information wirelessly to patient support apparatus 20 and to receive information wirelessly from patient support apparatus 20. In some instances, the information received from patient support apparatus 20 is forwarded to room interface board 58 via nurse call transceiver 100, while in other instances, the information received from patient support apparatus 20 is stored in memory 94. In still other instances, the information received from patient support apparatus 20 is both stored in memory 94 and forwarded to room interface board 58, which may in turn forward the information to nurse call system 60 and/or other devices in communication with room interface board 58.

When patient support apparatus 20 is positioned within a bay 102 and in normal communication with headwall unit 66, both of the transceivers 86 and 88 are in communication with patient support apparatus 20, and at least one of transceivers 86, 88 may also be in communication with a medical device 112 and/or a mobile electronic device 116 carried by, or associated with, a caregiver 114. If patient support apparatus 20 is positioned outside of the bay area 102, first transceiver 86 will not be able to communicate with patient support apparatus 20 because first transceiver 86 uses infrared signals, which are line-of-sight signals, and first transceiver 86 is set up such that its line-of-sight signals are only detectable by the patient support apparatus 20 when the patient support apparatus 20 is positioned within the corresponding bay 102, or a portion of that bay 102. Accordingly, when controller 92 determines that first transceiver 86 is able to successfully communicate with a patient support apparatus 20, it concludes that the patient support apparatus 20 is positioned adjacent to the headwall unit 66.

Second transceiver 88 is able to communicate with patient support apparatus 20 when patient support apparatus 20 is positioned outside of bay area 102 because second transceiver 88 is a Bluetooth transceiver that uses radio frequency (RF) waves that are not line-of-sight. Accordingly, none of patient support apparatus 20, medical devices 112, and/or mobile electronic device 116 needs to be in bay area 102 to communicate with second transceiver 88. However, the power levels of the Bluetooth communication used by second transceiver 88 are set such that patient support apparatus 20, medical devices 112, and/or mobile electronic device 116 are not generally able to communicate with second transceiver 88 when these devices are positioned outside of the room in which the headwall unit 66 is positioned. As a result, when controller 92 establishes communication with any patient support apparatus 20, medical device 112, and/or mobile electronic device 116, controller 92 knows that such devices are currently positioned within the same room as the headwall unit 66 (or very close by). Further, when controller 92 establishes communication with patient support apparatus 20 using first transceiver 86, controller 92 knows that patient support apparatus 20 is currently positioned within the bay area 102, and controller 92 is thereby able to confirm its position within a particular room using two sources of information.

Headwall unit 66 is adapted, in some embodiments, to be a repository of information relating to the patient associated with patient support apparatus 20, the patient support apparatus 20 itself, and one or more medical devices 112 used in conjunction with the treatment of the patient. As such, headwall unit 66 is configured to establish communications with patient support apparatuses 20 and medical devices 112 when these devices are brought into a room. After being brought into the room, data from these devices is transmitted to headwall unit 66 and, in some embodiments, stored locally in memory 94, and in other embodiments is transmitted to a remote location (either in lieu of, or in addition to, storing the data locally).

Second transceiver 88 is configured to periodically transmit a beacon signal, such as, but not limited to, approximately once every second. When a patient support apparatus 20, medical device 112, or mobile electronic device 116 moves into the room in which the headwall unit 66 is positioned, these devices receive the beacon signal and respond thereto. The beacon signal includes an identifier of that particular headwall 66 and the devices (patient support apparatus 20, medical device 112, and mobile electronic device 116) automatically establish communication links with the headwall unit 66 in response to the beacon signal. That is, headwall unit 66 is configured, in at least some embodiments, to automatically establish a communication link 118 between second transceiver 88 and patient support apparatus 20 when patient support apparatus 20 enters the room; to automatically establish a communication link 120 between second transceiver 88 and medical device 112 when the medical device enters the room and/or is turned on; and to automatically establish a communication link 122 between second transceiver 88 and a mobile electronic device 116 carried by, or associated with, a caregiver 114 (FIG. 4).

As was noted previously, in some modified embodiments, headwall unit 66 includes an auxiliary transceiver 96 that automatically establishes a communication link 124 with medical devices 112 and/or a caregiver detector 98 that automatically established a communication link 126 with mobile electronic device 116 when the device 116 enters the room. In such modified embodiments, links 120 and 124 may both be established between headwall unit 66 and medical devices 112, or only a single one of these links. Similarly, in such modified embodiments, links 122 and 126 may both be established between headwall unit 55 and mobile electronic device(s) 116, or only a single one of these links In some other embodiments to be discussed in more detail below, no link is established directly between medical devices 112 and headwall unit 66, and/or no link is established between mobile electronic device 116 and headwall unit 66. Instead, the medical devices 112 and/or mobile electronic devices 116 communicate with patient support apparatus 20 and patient support apparatus 20 communicates their data to headwall unit 66 via link 118 (or, in some cases, via the link 128 between patient support apparatus 20 and first transceiver 86).

Regardless of which specific communication links are established in a particular embodiment of headwall unit 66, the establishment of at least communication links 118 and 128 takes place automatically without requiring any steps on the part of a caregiver that are specific to this process. In other words, the caregiver does not need to press a button, flip a switch, or manipulate any controls on patient support apparatus 20 or headwall unit 66 to establish links 118 and 128. Instead, the mere positioning of patient support apparatus 20 within range of first and second transceivers 86 and 88 automatically causes patient support apparatus 20 to establish communication links with these devices. In some instances, depending on the design and/or settings of medical devices 112 and mobile electronic device 116, the establishment of links 120 and 122 may also be implemented automatically.

In those implementations of headwall system 156 where one or more rooms in a healthcare facility contain multiple headwall units 66 (see, e.g., room 134 of FIG. 5), second transceiver 88 may initially establish a communication link 118 with a patient support apparatus 20 when entering a room that is not the patient support apparatus 20 that is ultimately parked in front of the headwall unit 66 of second transceiver 88. In other words, when patient support apparatus 20 is initially moved into a room with multiple headwall units 66, the patient support apparatus may be able to communicate with the second transceiver 88 of both headwall units 66. Multiple communication links 118 may therefore be initially established. However, once the patient support apparatus 20 is moved to its intended bay area 102, the patient support apparatus 20 establishes link 128 with first transceiver 86, and first transceiver 86 transmits to the patient support apparatus the unique identifier 104 corresponding to the headwall unit 66 of that particular bay area 102. The patient support apparatus 20 uses this specific identifier to determine which of the multiple headwall units 66 it is supposed to have second communication link 118 with, and disestablishes any second communication links 118 it may have established with the other headwall unit(s) 66 that do not have the specific identifier it received via communication link 128. The result is that patient support apparatus 20 ends up having a single communication link 118 and a single communication link 128 with only one (and the same) headwall unit 66.

Regardless of the specific links implemented, when patient support apparatus 20 is positioned in front of a headwall unit 66 in bay area 102, it communicates both messages to be relayed to room interface board 58 (which then routes them accordingly) and data to be stored within headwall unit 66. The data to be stored within headwall unit 66 includes data about the status of one or more sensors, switches, actuators, and other components of patient support apparatus 20, as well as data about the patient associated with patient support apparatus 20. The specific data sent by patient support apparatus 20 to be stored by headwall unit 66 may vary widely from embodiment to embodiment. In general, this data may include any one or more of the following items of information: the status of a brake on patient support apparatus 20, the status of an exit detection system of patient support apparatus 20 (e.g. whether armed or not); the status of siderails 34 (e.g. whether raised or not); the height of support deck 30; the angle of head section 42; any of one or more weights detected or calculated by a scale system on board patient support apparatus 20 (e.g. a tare weight, patient weight, object weight, etc.); a mobility score or index of the patient; one or more vital signs of the patient; a time at which the patient was last turned; any data from a powered mattress positioned on board patient support apparatus 20 (e.g. inflation pressure, therapies implemented via the powered mattress, patient movement detected by the mattress, etc.); a time since the patient last exited patient support apparatus 20; an amount of time the patient spent off patient support apparatus 20; one or more measurements related to a patient's sleep (e.g. quantity, quality, start time, end time, etc.); interface pressures between the patient and the mattress, or other surface, on which the patient is supported; a cleaning status of patient support apparatus 20; an identity of the patient (as detected by the patient support apparatus 20 or entered via a caregiver into a memory on board the patient support apparatus); and still other data gathered from one or more components of patient support apparatus 20.

The sensors and components used to generate any of the above-identified information may vary from patient support apparatus to patient support apparatus, and some patient support apparatuses may be able to detect and transmit more information to headwall unit 66 than other patient support apparatuses. Although other constructions may be used, the following chart identifies commonly assigned U.S. patent applications/patents disclosing patient support apparatuses constructed to detect the identified data. Any of these constructions may be used by patient support apparatus 20 to detect the aforementioned data that is forwarded to headwall unit 66, although other constructions may also be used. Each of these commonly assigned patent applications is incorporated herein by reference in their entirety. Still other data may be detected and forwarded to headwall unit 66 beyond the data identified above and the data detected in the following patents and patent applications.

| Patent/App. | Filing Date | Title | Data Detected |
| --- | --- | --- | --- |
| 5,276,432 | Jan. 15, 1992 | Patient Exit Detection Mechanism for Hospital Bed | Patient's location (center of gravity) |
| 7,699,784 | Jul. 5, 2007 | System for Detecting and Monitoring Vital Signs | Patient's heart rate, breathing rate, and other vital signs |
| 9,320,444 | Mar. 14, 2014 | Patient Support Apparatus with Patient Information Sensors | Patient sleep quantity, quality, and other sleep parameters; patient weight |
| 61/449,182 | Mar. 4, 2011 | Sensing System for Patient Supports | Patient interface pressures, vital signs, |
| 14/692,871 | Apr. 22, 2015 | Person Support Apparatus with Position Monitoring | Patient movement |
| 14/873,734 | Oct. 2, 2015 | Person Support Apparatus with Motion Monitoring | Patient and object weights, movement, and position |
| 14/928,513 | Oct. 30, 2015 | Person Support Apparatus with Patient Mobility Monitoring | A patient's activity, time out of bed, number of steps, and other activity data |
| 14/578,630 | Dec. 22, 2014 | Video Monitoring System | Patient turns, bed sore assessment scores, eating and sleeping, exit detection system status, etc. |
| 15/346,779 | Nov. 9, 2016 | Person Support Apparatus with Acceleration Detection | Patient vital signs, position, movement |
| 15/809,351 | Nov. 10, 2017 | Patient Support Apparatuses with Mobility Assessment | Patient mobility score and/or assessments |
| 15/709,586 | Sep. 20, 2017 | Systems and Methods for Determining the Usability of Person Support Apparatuses | Cleanliness and/or usability status of a patient support apparatus |

In addition to the aforementioned data, headwall unit 66 is adapted to receive data from one or more medical devices 112 positioned within the room and associated with the patient on patient support apparatus 20. In some embodiments, this data is communicated to patient support apparatus 20 first, which then forwards the data to headwall unit 66 via communication link 118 (or, in some cases, link 128). In some embodiments, patient support apparatus 20 is constructed with an open electronic framework for allowing third party medical devices to control a portion of the screen space of patient support apparatus 20 and/or to utilize the patient support apparatuses communication abilities for forwarding their data to a remote location (e.g. a remote electronic medical records (EMR) server 130). In one such embodiment, patient support apparatus 20 is constructed to communicate with medical devices 112 in any of the manners disclosed in commonly assigned U.S. patent application Ser. No. 62/513,641 filed Jun. 1, 2017, by inventors Krishna Bhimavarapu et al. and entitled PATIENT CARE DEVICES WITH OPEN COMMUNICATION, the complete disclosure of which is incorporated herein by reference. Other types of communication methods may be used between medical devices 112 and the patient support apparatus 20.

Regardless of the specific communication method between patient support apparatus 20 and the one or more medical devices 112, patient support apparatus 20 is adapted to forward the data received from the medical device(s) 112 to headwall unit 66, as well as to the destination intended by the medical device 112, if any, (e.g. EMR server 130). For some medical devices 112, this forwarding of medical device data to headwall unit 66 takes place automatically without any prompting from the medical device 112. For such medical devices, patient support apparatus 20 copies the received data and forwards it to headwall unit 66 unbeknownst to the medical device 112. Other types of medical devices 112 may be constructed such that they knowingly send their data to headwall unit 66, and in such cases patient support apparatus 20 follows the instructions received from the medical device with respect to the forwarding of the medical device's data to headwall unit 66. In still other cases, a particular medical device 112 may not forward any data until a request for the data is received from the patient support apparatus 20. In these situations, headwall unit 66 forwards a request for the data to patient support apparatus 20 which, in turn, passes the request onto the one or more medical devices 112 it is in communication with. The medical device 112 responds by sending the data to patient support apparatus 20, which then forwards the data to headwall unit 66.

Depending upon the particular medical devices 112 that are being used with a particular patient, some medical devices 112 may be configured to transmit their data to headwall unit 66 directly using communication link 120. In such instances, the medical device 112 may or may not forward any of its data to patient support apparatus 20.

As was noted previously, in some embodiments, headwall unit 66 stores all of the data it receives from patient support apparatus 20 and medical devices 112 locally within memory 94. In other embodiments, headwall unit 66 copies the data locally into memory 94 and also sends a copy of the data to a remote location via network transceiver 90, such as a headwall server 132 that is in communication with healthcare facility network 106. In still other embodiments, headwall unit 66 also forwards the received data to EMR server 130 in addition to, or in lieu of, the forwarding of the data to headwall server 132.

The types of medical devices 112 which headwall unit 66 and/or patient support apparatus 20 communicate with may vary widely. Some examples of these types of medical devices 112 include, but are not limited to, the following: a ventilator, an infusion pump; a pulse oximeter; a vital sign(s) detector; a Deep Vein Thrombosis (DVT) cuff (or other DVT device); a patient identification device (e.g. an RF ID tag, bracelet, or the like); a pulse wave velocity detector; a sleep detector; a thermal control system; and others. One suitable example of a pulse wave velocity detector that may be used with the patient and that forwards its data to headwall unit 66 is disclosed in commonly assigned U.S. patent application Ser. No. 14/884,222 filed Oct. 15, 2015, by inventors Sean Hadley et al. and entitled SYSTEMS AND METHODS FOR DETECTING PULSE WAVE VELOCITY, the complete disclosure of which is incorporated herein by reference. One suitable example of a thermal control system that may be used with the patient and that forwards its data to headwall unit 66 is disclosed in commonly assigned U.S. patent application Ser. No. 14/282,383 filed May 20, 2014, by inventors Christopher Hopper et al. and entitled THERMAL CONTROL SYSTEM, the complete disclosure of which is incorporated herein by reference.

Controller 92 of headwall unit 66 is programmed to time stamp the data it receives from patient support apparatus 20 and medical devices 112 and store the time stamp with the data (whether locally in memory 94 or remotely). Controller 92 is also programmed to store the data in such a way so that the data correlates to a specific patient support apparatus 20, a specific bay 102, a specific patient, and/or a specific medical device 112. Further, in at least some embodiments, the "specific patient" information is stored in headwall unit 66 in a generic manner that does not identify a private identity of the patient. For example, in some embodiments, controller 92 identifies the specific patient in a generic manner, such as "patient X associated with patient support apparatus Y." Or, because patient support apparatuses 20 typically have multiple patients associated with them over time, controller 92 may identify the specific patient as "patient X who is/was associated with patient support apparatus Y at time(s) T."

In some embodiments, controller 92 is programmed to delete the data stored in memory 94 whenever a new patient is assigned to patient support apparatus 20. In such embodiments, controller 92 may avoid storing any patient-identification data with the understanding that all of the stored data generically correlates to the "current patient." In any of the aforementioned embodiments, controller 92 is adapted to store the received data in a manner that leaves out the actual identity of the patient (e.g. Mary Smith) such that any unauthorized access to headwall unit 66 does not reveal private data that can be correlated to a humanly identifiable person. In still other embodiments, controller 92 is programmed to store the data it receives from patient support apparatus 20 and medical devices 112 with the actual identity of the patient, but does so utilizing security measures built into headwall unit 66 and its communication links that ensure that this data meets all applicable medical data privacy standards.

Figure 5:
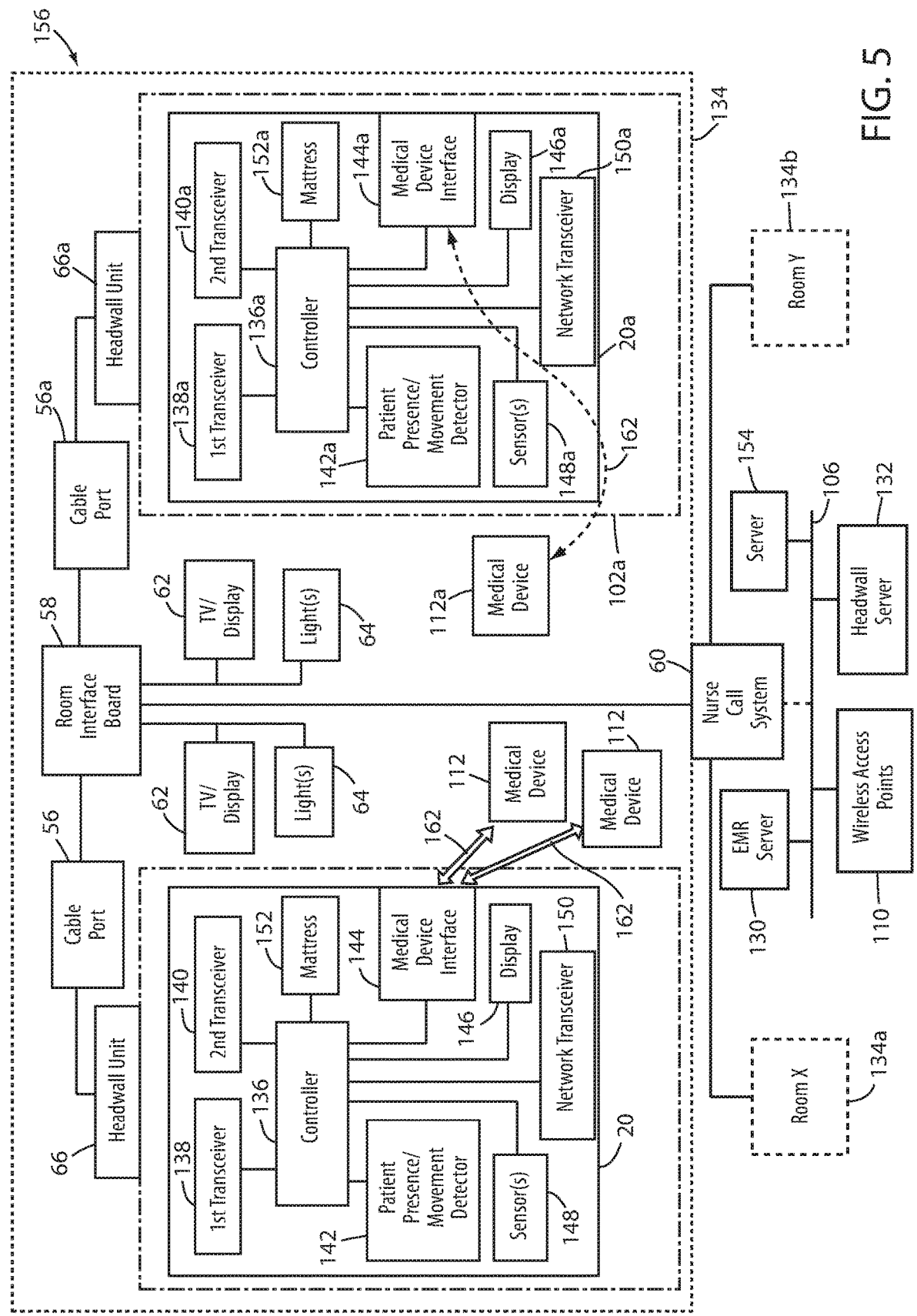
FIG. 5 is a block diagram of the headwall system of FIG. 4 showing its implementation with multiple headwall units and in multiple rooms of a healthcare facility.

FIG. 5 illustrates in greater detail various internal components of patient support apparatus 20, as well as more of the healthcare IT infrastructure 52 that may be present in a particular installation of headwall system 156. FIG. 5 also illustrates an illustrative non-private room 134 of a healthcare facility and the manner in which the headwall units 66 of the room 134 may interact with their associated patient support apparatuses 20 and the healthcare IT infrastructure. Although FIG. 5 illustrates two identical patient support apparatuses 20 and 20a, it will be understood that this is merely for purposes of explanation and that the particular types of patient support apparatuses 20 used with headwall units 66 may vary within a healthcare facility.

Patient support apparatus 20 includes a controller 136 in communication with a first transceiver 138, a second transceiver 140, a patient presence/movement detector 142, a medical device interface 144, a display 146, one or more sensors 148, a network transceiver 150, and, in some cases, a powered mattress 152. Controller 136, like controller 92 of headwall unit 66, includes any and all electrical circuitry and components necessary to carry out the functions and algorithms described herein, as would be known to one of ordinary skill in the art. Generally speaking, controller 136 may include one or more microcontrollers, microprocessors, and/or other programmable electronics that are programmed to carry out the functions described herein. The other electronic components may include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions within patient support apparatus 20, or they may reside in a common location within patient support apparatus 20. When physically distributed, the components may communicate using any suitable serial or parallel communication protocol, such as, but not limited to, CAN, LIN, Firewire, I-squared-C, RS-232, RS-465, universal serial bus (USB), etc. The instructions followed by controller 136 in carrying out the functions described herein, as well as the data necessary for carrying out these functions, are stored in one or more accessible memories (not shown).

Patient presence/movement detector 142 is adapted to automatically detect whether or not a patient is currently present on patient support apparatus 20, as well as, in some instances, to detect movement and/or the position of the patient when the patient is supported on patient support apparatus 20. The specific components of patient presence detector 142 and/or manner in which it detects a patient's presence/absence/movement/location may vary from embodiment to embodiment. In one embodiment, patient presence detector 142 includes a plurality of force sensors, such as, but not limited to, load cells that detect the weight and/or center of gravity of the patient. Illustrative manners in which such force sensors can be used to detect the presence and absence of a patient, as well as the center of gravity of the patient, are disclosed in the following commonly assigned U.S. patent references: U.S. Pat. No. 5,276,432 issued to Travis and entitled PATIENT EXIT DETECTION MECHANISM FOR HOSPITAL BED; and U.S. patent application Ser. No. 62/253,167 filed Nov. 10, 2015, by inventors Marko Kostic et al. and entitled PERSON SUPPORT APPARATUSES WITH ACCELERATION DETECTION, the complete disclosures of both of which are incorporated herein by reference. Other algorithms for processing the outputs of the force sensors may also be used for detecting a patient's presence and absence.

Patient presence detector 142 may alternatively be implemented using one or more thermal sensors mounted to patient support apparatus 20 that detect the absence/presence of the patient and/or the position of the patient's head on patient support apparatus 20. Further details of such a thermal sensing system are disclosed in commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosure of which is incorporated herein by reference.

In still other embodiments, patient presence detector 142 detects the absence/presence/movement/location of a patient using one or more of the methods disclosed in commonly assigned U.S. patent application Ser. No. 14/928,513 filed Oct. 30, 2015, by inventors Richard Derenne et al. and entitled PERSON SUPPORT APPARATUSES WITH PATIENT MOBILITY MONITORING, the complete disclosure of which is also hereby incorporated herein by reference. In yet other embodiments, patient presence detector 142 includes one or more video cameras for detecting the patient's presence, absence, movement, and/or position, such as disclosed in commonly assigned U.S. patent application Ser. No. 14/578,630 filed Dec. 22, 2014, by inventors Richard Derenne et al. and entitled VIDEO MONITORING SYSTEM, the complete disclosure of which is also hereby incorporated herein by reference. In yet another alternative embodiment, the presence, absence, movement and/or position of a patient is detected using a pressure sensing mat. The pressure sensing mat is positioned on top of the mattress or support deck 30, such as is disclosed in commonly assigned U.S. patent application Ser. No. 14/003,157 filed Mar. 2, 2012, by inventors Joshua Mix et al. and entitled SENSING SYSTEM FOR PATIENT SUPPORTS, the complete disclosure of which is also incorporated herein by reference. In still other embodiments, patient presence detector 142 may take on still other forms.

First transceiver 138 of patient support apparatus 20 is adapted to communicate with first transceiver 86 of headwall unit 66. Thus, in some embodiments, first transceiver 138 is an infrared transceiver that communicates with headwall unit 66 only when patient support apparatus is within line-of-sight communication range of first transceiver 86 (e.g. within the corresponding bay 102). Second transceiver 140 of patient support apparatus 20 is adapted to communicate with second transceiver 88 of headwall unit 66. Thus, in some embodiments, second transceiver 140 is a Bluetooth transceiver. Network transceiver 150 of patient support apparatus 20 is adapted to communicate with the wireless access points 110 of healthcare computer network 106 and, in some embodiments, is a WiFi transceiver. Alternatively, network transceiver 150 may take on any of the forms disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference.

Medical device interface 144 is a wired and/or wireless interface adapted to communicate via a communication link 162 with one or more medical devices 112 (FIG. 5). When communication link 162 is a wired link, interface 144 may include a Universal Serial Bus (USB) port, an Ethernet port, an RS-232 port, and/or another type of port enabling a cable from the medical device 112 to be inserted thereinto so that communication between patient support apparatus 20 and the medical device 112 takes place over the cable. When communication link 162 is a wireless link, interface 144 may include a ZigBee transceiver, a Bluetooth transceiver, or another type of wireless transceiver that enables wireless communication directly between patient support apparatus 20 and the medical device(s) 112. Further details regarding several illustrative manners in which medical devices may communicate with a patient support apparatus are disclosed in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES; and U.S. patent application Ser. No. 62/513,641 filed Jun. 1, 2017, by inventors Krishna Bhimavarapu et al. and entitled PATIENT CARE DEVICES WITH OPEN COMMUNICATION, the complete disclosures of both of which are incorporated herein by reference.

In some embodiments, display 146 is positioned on patient support apparatus on footboard 32 and is part of footboard user interface 50*a*. In other embodiments, display 146 is positioned elsewhere, such as one siderails 34 as part of caregiver user interfaces 50*b*. In still other embodiments, display 146 is positioned elsewhere. In some embodiments, patient support apparatus 20 includes multiple displays 146. In any of these embodiments, display 146 may be a touch screen display, a non-touch screen display, or any other type of display capable of displaying data gathered from patient support apparatus 20 and/or medical devices 112.

Mattress 152 may be a powered mattress that includes one or more inflatable chambers that are inflated under the control of controller 136 of patient support apparatus 20. In some embodiments, mattress 152 is configured to apply one or more therapies to a patient (e.g. a percussion therapy) and/or to assist in automatically turning a patient. Still further, in some embodiments, mattress 152 may include one or more vital sign sensors built into it that detect one or more of the patient's vital signs, as well as one or more pressure sensors that detect fluid pressure inside of the chambers and/or interface pressure between the patient and the mattress. When mattress 152 includes one or more these features, data from the mattress is communicated to controller 136 which forwards some or all of the data to headwall unit 66 for storage in memory 94 (and/or forwards to a remote location). An illustrative mattress 152 suitable for use with patient support apparatus 20 that includes many of these features is disclosed in commonly assigned U.S. patent application Ser. No. 13/836,813 filed Mar. 15, 2013, by inventors Patrick Lafleche et al. and entitled INFLATABLE MATTRESS AND CONTROL METHODS, the complete disclosure of which is incorporated herein by reference. Other types of mattresses 152 may, of course, be used.

Sensor(s) 148 of patient support apparatus 20 (FIG. 5) may take on a variety of different forms. In some embodiments, as will be discussed in greater detail below, sensor(s) 148 include any one or more of the following: a brake sensor adapted to detect whether or not a caregiver has applied a brake to patient support apparatus 20; a height sensor adapted to detect the height of support deck 30 (and/or detect whether support deck 30 is at its lowest height or not); siderail sensors adapted to detect whether siderails 34 are in their raised or lowered orientations; an exit detection status sensors adapted to detect whether an exit detection system on board patient support apparatus 20 is armed or not; a microphone adapted to detect the voice of patient positioned on patient support apparatus 20 so that the patient can communicate aurally with a remotely positioned caregiver (via nurse call system 60); and/or another type of sensor.

It will be understood that patient support apparatuses 20 include more components than those shown in FIG. 5, and that controller 136 may control more than the components shown in FIG. 5. For example, as noted with respect to FIG. 1, patient support apparatus 20 includes a plurality of user interfaces 50. Those user interfaces may be in direct communication with controller 136 and/or under the control of controller 136, or those user interfaces 50 may be under the control of a separate controller that is, in turn, in communication with controller 136. Patient support apparatus 20 may also include an exit detection system that is under the control of controller 136, or that includes its own controller that communicates with controller 136. One such suitable exit detection system is disclosed in commonly assigned U.S. Pat. No. 5,276,432 issued to Travis and entitled PATIENT EXIT DETECTION MECHANISM FOR HOSPITAL BED, which is incorporated herein by reference, although other types of exit detection systems may be included with patient support apparatus 20. Still other components may be present on patient support apparatus 20 and under the control of controller 136 or another controller onboard patient support apparatus 20.

Patient support apparatus 20 is depicted as being located in a particular room 134 of a healthcare facility in FIG. 5. The healthcare facility may include additional rooms 134*a*, 134*b*, etc. that are similar to room 134. That is, each room may include one or more headwall units 66, and each headwall unit 66 is in communication with a cable port 56 and the room interface board 58 for that particular room. The room interface boards 58, in turn, are in communication with room lights 64 and TV/display 62 for that particular room. Still further, each room interface board 58 is coupled to the nurse call system 60. The nurse call system 60, in some embodiments, is in communication with the healthcare facility computer network 106.

Healthcare facility computer network 106 includes a plurality of servers, such as, but not limited to, EMR server 130 and headwall server 132. One or more additional servers 154 may also be included, such as, but not limited to, an Internet server and/or an Internet gateway that couples network 106 to the Internet, thereby enabling server 132, headwall units 66, patient support apparatuses 20, and/or other applications on network 106 to communicate with computers outside of the healthcare facility, such as, but not limited to, a geographically remote server operated under the control of the manufacturer of patient support apparatuses 20 and/or headwall units 66. Another type of server that may be included with computer network 106 is a location server (not shown) that is adapted to monitor and record the current locations of patient support apparatuses 20, patients, and/or caregivers within the healthcare facility. Such a location server communicates with the patient support apparatuses 20 and/or headwall units 66 via access points 110 and network transceivers 90 and 150.

Network 106 may also include a conventional Admission, Discharge, and Tracking (ADT) server that allows patient support apparatuses 20 and/or headwall units 66 to retrieve information identifying the patient assigned to a particular patient support apparatus 20. Still further, healthcare network 106 may further include one or more conventional work flow servers and/or charting servers that assign, monitor, and/or schedule patient-related tasks to particular caregivers, and/or one or more conventional communication servers that forward communications to particular individuals within the healthcare facility, such as via one or more portable devices (smart phones, pagers, beepers, laptops, etc.). The forwarded communications may include data and/or alerts that originate from patient support apparatuses 20 and/or headwall units 66.

It will also be understood by those skilled in the art that still more modifications to network 106 may be made beyond those listed herein. As but one example, it will be understood that, although FIGS. 4 & 5 shows nurse call system 60 coupled to network 106, this may be modified. Still other modifications are possible.

Figure 6:
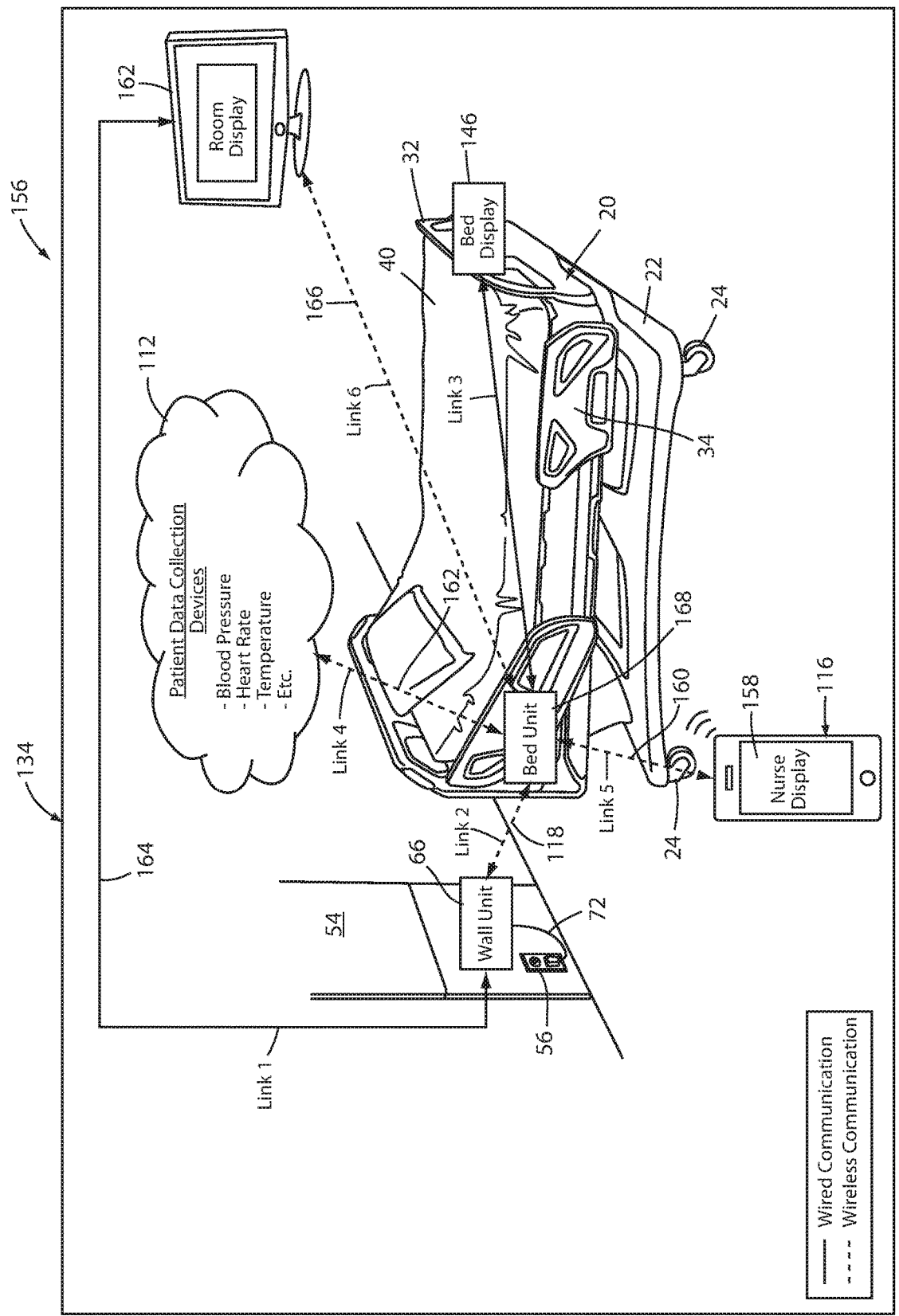
FIG. 6 is a perspective view of the headwall system of FIG. 4 showing a display feature for displaying medical data relating to a patient associated with the patient support apparatus.

FIG. 6 illustrates an illustrative manner in which headwall system 156 operates in order to display relevant data to a healthcare worker. Headwall system 156 includes headwall unit 66 and the structures disclosed and discussed above with respect to FIGS. 4 and 5. The "bed unit" 168 shown in FIG. 6 refers to controller 136, medical device interface 144, and the transceivers of patient support apparatus 20 (e.g. transceivers 138, 140, 150). Headwall system 156 collects data from patient support apparatus 20 and any associated medical devices 112 and automatically displays the data at a centralized display location with room 134. In the illustrated embodiment, the displayed data is displayed at any one or more of the following locations: a display 158 built into mobile electronic device 116, one or more of the displays 146 of patient support apparatus, one of the TV/displays 62 associated with the room 134, and/or a display built into headwall unit 66 (not shown). The displayed data includes any of the aforementioned data that is forwarded to headwall unit 66 and stored therein (and/or forwarded to a remote location).

When a caregiver initially enters room 134, second transceiver 140 of patient support apparatus 20 transmits a beacon message (as it periodically does) and this beacon message is received by the mobile electronic device 116. The detection of this beacon message is carried out, in some embodiments, using conventional beacon detection technology. For example, if mobile electronic device 116 is a smart phone, tablet, or other computer running an operating system developed by Apple Corporation of Cupertino, California, second transceiver 140 may utilize the iBeacon protocol, which is based on Bluetooth Low Energy (BLE). If mobile electronic device 116 is an Android based device utilizing any of the various Android operating systems, the mobile electronic device 116 may utilize a conventional beacon detecting app downloaded from the Google Play store, an Eddystone beacon, or another type of beacon pre-installed on the device 116 or downloaded to it. Other technologies for broadcasting and detecting the beacon signals may also be used, and mobile electronic device 116 may execute an operating system other than an Apple or Android based operating system.

After second transceiver 140 has established a communication link 160 (FIG. 6) between patient support apparatus 20 and mobile electronic device 116, controller 136 of patient support apparatus 20 requests from mobile electronic device 116 any display preferences that the owner of (or caregiver associated with) mobile electronic device 116 has saved on their mobile electronic device 116. For example, a first caregiver may store on mobile electronic device 116 information indicating that he or she wants data from headwall unit 66 to automatically be displayed on the display 146 of patient support apparatus 20 that is located on the footboard of the patient support apparatus 20. Another caregiver may store preference data on his or her mobile electronic device 116 indicating that he or she prefers to have the same data automatically displayed on the TV/display 62 mounted in the room 134. Still another caregiver may prefer the data to be displayed on the display 158 of the mobile electronic device 116. These preferences are forwarded by controller 136 of patient support apparatus 20 to controller 92 of headwall unit 66, which uses the information to determine where to route the data to be displayed.

In addition to identifying which display the caregiver prefers, the preference data stored on mobile electronic device 116 may store other preference data, such as preference data indicating which data to display, what format to display the data in, and/or how much data to display. For example, some caregivers may only be interested in vital sign readings of a patient, others may have an interest in one or more states of patient support apparatus 20, and others may have an interest in the data from certain medical devices 112, but not others of the medical devices 112. Controller 92 of headwall unit 66 reads this preference data and displays the desired data on the desired displays within room 134.

In some embodiments, mobile electronic device 116 includes an authorization identifier that indicates what level of authorization the associated caregiver possesses. Headwall unit 66 uses this authorization identifier to determine what stored data that particular caregiver has access to. In some embodiments, certain caregivers may only be authorized to view a restricted subset of the data stored by, or on, headwall unit 66. In such embodiments, controller 136 of patient support apparatus 20 forwards the authorization identifier to headwall controller 92 and headwall controller 92 uses the identifier to determine what data to display for this particular caregiver based on his or her authorization level, and what data not to display for this particular caregiver based on his or her authorization level.

Although the transmission of a beacon signal that is detected by mobile electronic device 116 has been described above as a beacon signal that originates from second transceiver 140 of patient support apparatus 20, it will be understood that this aspect of headwall system 156 may be modified such that the beacon signal originates from second transceiver 88 of headwall unit 66. When so modified, the beacon signal is communicated directly to the mobile electronic device 116 and is used to establish communication link 122 (FIG. 4). When mobile electronic device 116 communicates with headwall unit 66 via communication link 122, the exchanged messages circumvent patient support apparatus 20 and there is no need for patient support apparatus 20 to act as an intermediary between mobile electronic device 116 and headwall unit 66. In some embodiments, mobile electronic device 116 may establish both communication links 160 and 122 and utilize either or both of these at different times and/or for different messages. In the embodiment shown in FIG. 6, however, messages exchanged between mobile electronic device 116 and headwall unit 66 are passed through patient support apparatus 20 via links 118 and 160.

Controller 92 of headwall unit 66 reacts to the display preference data communicated from mobile electronic device 116 by determining what data to display, where to display it, and then sending the data to the corresponding display. If the data is to be displayed on TV/display 62, controller 92 sends the data thereto in one of three different manners, depending upon how system 156 is implemented in a particular healthcare facility. In a first embodiment, controller 92 sends the data to be displayed on TV/display 62 by transmitting the data over a communication link 164. Communication link 164 includes cable 72, cable port 56, room interface board 58, and one or more wires coupling room interface board 58 to TV/display 62. In an alternative embodiment, TV/display 62 is equipped with a wireless transceiver and one of the transceivers of headwall unit 66 wirelessly transmits the data directly to the wireless transceiver of TV/display 62. In some embodiments, the wireless transceiver is a conventional wireless dongle that is inserted into a port of TV/display 62 and that enables wireless communication with appropriately configured wireless devices (e.g. headwall unit 66). In still another embodiment, controller 92 of headwall unit 66 sends the data to be displayed on TV/display 62 first to controller 136 of patient support apparatus 20, which in turn forwards the data wirelessly directly to TV/display 62 via a wireless link 166. Wireless link 166 may utilize second transceiver 140 of patient support apparatus 20, network transceiver 150 of patient support apparatus 20, or some other transceiver of patient support apparatus 20.

If the data to be displayed by headwall unit 66 is to be displayed on a display of patient support apparatus 20, controller 92 of headwall unit 66 transmits the data to controller 136 of patient support apparatus 20 with the instruction to display the data on the corresponding display (e.g. display 146). If the data to be displayed by headwall unit 66 is to be displayed on the display 158 of the mobile electronic device 116 itself, controller 92 of headwall unit 66 transmits the data to mobile electronic device 116, either directly via communication link 122, or through patient support apparatus 20 via communication links 118 and 160. In some embodiments, a caregiver may prefer to see some data on a first display and other data on another display. In such situations, this multi-display preference is included within the stored preferences of mobile electronic device 116, is communicated to controller 92 of headwall unit 66, and causes controller 92 to divide the data in the specified manner for displaying the data on multiple displays within room 134.

In the illustrated embodiment, controller 92 of headwall unit 66 is configured to automatically display the data on the preferred displays in response to the mobile electronic device 116 establishing either communication link 122 or 160. In some embodiments, mobile electronic device 116 may include a preference setting (forwarded to headwall unit 66) indicating that such data is only to be displayed when the caregiver activates a button, or other control, on the mobile electronic device 116. In such embodiments, the display of data may be delayed until the caregiver activates the control on his or her mobile electronic device 116.

It will be understood that the data displayed by headwall unit 66 on one or more of the displays positioned within room 134 includes not only previously stored data, but also current data that is currently being sent to headwall unit 66 from patient support apparatus 20 and/or one or more medical devices 112. Thus, for example, if one of medical devices 112 is a vital signs measuring device, the current readings from the device 112 are forwarded to headwall unit 66, which then forwards them for display on the preferred display of the particular caregiver who is in the room 134. In this manner, the caregiver is able to see on the preferred display the patient's current vital sign readings.

It will also be understood that the displayed data may come from multiple sources, yet still be displayed on a common display. For example, headwall unit 66 may display on TV/display 62 data from one or sensors 148 on board patient support apparatus 20, data from a first medical device 112, and data from a second medical device 112. As was noted previously, the format for displaying this multi-sourced data can be selected by a caregiver and input into the preference setting stored on board mobile electronic device 116.

In some embodiments, headwall unit 66 is configured to display one or more items of data regardless of whether or not a caregiver is positioned within room 134. The particular data items to be displayed can be configured by an authorized technician of the healthcare facility. Such configuration can take place locally or centrally via headwall server 132. In such embodiments, when a caregiver's mobile electronic device 116 is detected within a room 134, headwall unit 66 is configured to switch to displaying the data in the format and location preferred by that particular caregiver. In other words, the presence of the caregiver's mobile electronic device 116 in the room 134 overrides the display preferences that are stored within headwall unit 66, and controller 92 of headwall unit 66 automatically switches to the caregiver's display preferences.

Some data communicated to patient support apparatus 20 and/or headwall unit 66 may be communicated infrequently, or may not be communicated at all unless specifically requested. For such situations, controller 92 of headwall unit 66 and/or controller 136 of patient support apparatus 20 are configured to automatically request updated data in response to the detection of a caregiver's mobile electronic device 116 within the room 134. In this manner, the caregiver is assured of seeing the most up-to-date data on the preferred display.

In some embodiments, mobile electronic device 116 includes software on-board that allows the caregiver to use controls on his or her mobile electronic device 116 to change the display of the data. For example, in some situations, there may be more data to display than can be displayed on the preferred display at the same time. Mobile electronic device 116 can be used in these situations by a caregiver to sort through the various data, review prior data, select data from a specific medical device, and/or otherwise control the data being displayed. In this manner, mobile electronic device 116 can be used as a sort of remote control device that dictates to headwall controller 92 how to change the display of the data beyond the manners specified in the preference settings.

Figure 7:
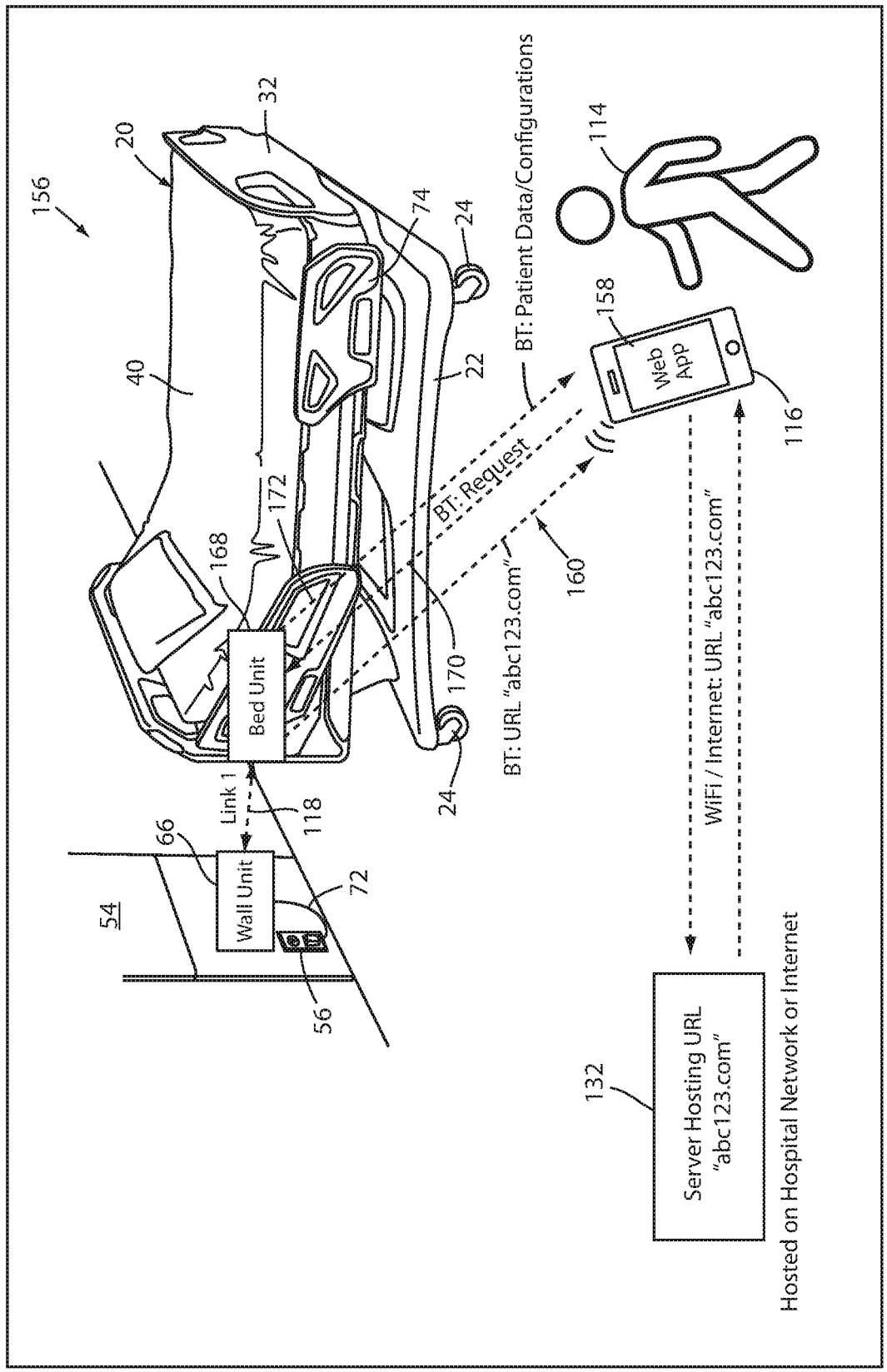
FIG. 7 is a perspective view of the headwall system of FIG. 4 showing the forwarding of a URL to a mobile electronic device carried by a healthcare provider.

FIG. 7 illustrates another aspect of headwall system 156. The aspect shown in FIG. 7 may be implemented separately from the functionality described with respect to FIG. 6, it may be used as a separate addition to the functionality described with respect to FIG. 6, or it may be used to implement the functionality of FIG. 6 as well as the functionality to be described below.

FIG. 7 illustrates in more detail one manner in which a caregiver mobile electronic device 116 may be used to control a headwall unit 66 and/or a bed unit 168 (e.g. controller 136, medical device interface 144, and the associated transceivers of patient support apparatus 20). Although FIG. 7 illustrates a mobile electronic device 116 communicating directly with bed unit 168 via communication link 160, it will be understood that the principles illustrated in FIG. 7 and discussed below can be applied to a communication link 120 that directly links mobile electronic device 116 to headwall unit 66.

In the embodiment shown in FIG. 7, mobile electronic device 116 and bed unit 168 are configured to use what is known as the "physical web." The physical web refers to the technology developed by Google, Inc. of Mountain View, California (now Alphabet, Inc.). Using this technology, bed unit 168 repetitively broadcasts a beacon, such as Bluetooth Low Energy beacon, that contains a Uniform Resource Locator (URL) associated with that particular patient support apparatus 20 and/or the particular headwall unit 66 adjacent to patient support apparatus 20. In some embodiments where mobile electronic device 116 is an Android device, the beacon is detected by the Nearby Notifications operating system level functionality that is built into the Android Lollipop operating system version (and other versions). In alternative embodiments, a conventional web browser in the mobile electronic device 116—such as, but not limited to, a Google Chrome browser—detects the beacon using commercially available functionality, such as, but not limited to, Google's Eddystone URL protocol. In still other embodiments, other types of beacons and beacon technology—such as, but not limited to, Apple's iBeacon technology—can be used to detect the broadcasted URL without requiring the user of the mobile electronic device 116 to install an app that is specific to patient support apparatus 20 and/or headwall unit 66. In some embodiments, patient support apparatus 20 and/or headwall unit 66 may include multiple beacons, each of which is compatible with a particular type of mobile electronic device 116.

When mobile electronic device 116 receives the URL from patient support apparatus 20, it provides a notification to the user of mobile electronic device 116 that it has detected a beacon associated with patient support apparatus 20 (or headwall unit 66). In some embodiments, the user is given the option to accept the notice and proceed to the URL, while in other embodiments the mobile electronic device 116 automatically connects to the URL. In either embodiment, mobile electronic device 116 uses conventional web browsing technology to go to the webpage, or other resource identified by the URL. In some embodiments, the URL identifies a resource at headwall server 132, which is part of the healthcare facility computer network 106. In other embodiments, the URL identifies a resource that is located on the Internet, in which case the mobile electronic device 116 couples to a wireless access point 110 of network 106 and proceeds to the resource via computer network 106's Internet gateway. In still other embodiments, the resource is located elsewhere.

Regardless of the specific location of the resource, it is a location accessible to mobile electronic device 116 and it delivers a web page, or the like, to mobile electronic device 116 that enables the mobile electronic device 116 to request, receive, and display the previously discussed data stored in headwall unit 66. More specifically, the URL provides mobile electronic device 116 with the resources and user interface to allow mobile electronic device 116 to control the requesting, receiving, and displaying of the previously mentioned data without requiring the user to install a special app. Instead, the requesting, receiving, and displaying of the data are all accomplished through a conventional web browser application installed on the mobile electronic device 116.

After connecting to the URL and retrieving the resources located there, the user of mobile electronic device 116 is presented with a user interface on display 158 of mobile electronic device 116. The user interface allows the user to retrieve any of the data stored in headwall unit 66 and display it on display 158 of mobile electronic device 116. The user interface also allows the user to send any of the data stored in headwall unit 66 to be displayed on one or more of the other displays positioned within room 134, such as TV/display 62 and/or patient support apparatus display 146. Still further, the user interface allows the user to update any desired data, change the content and/or format of the displayed data, and/or control other aspects of headwall unit 66 and/or patient support apparatus 20. As but one example, the user of mobile electronic device 116 can instruct headwall unit 66 to display the patient's current vital sign readings on TV/display 62 and to display the patient's turn history (a record of when they were turned on patient support apparatus 20) on display 146 of patient support apparatus 20. A virtually unlimited number of other configurations can be selected by the user of mobile electronic device 116.

The retrieval of the stored data by mobile electronic device 116 is carried out by sending a request for the data, as indicated by message 170 of FIG. 7. In the particular implementation shown therein, patient support apparatus controller 136 forwards the request message 170 to headwall unit 66 via communication link 118. Controller 92 of headwall unit 66 responds to the request by sending the requested data to controller 136 of patient support apparatus 20. Controller 136 of patient support apparatus 20 then forwards the response back to mobile electronic device 116, as indicated by message 172 in FIG. 7.

The URL broadcasted by patient support apparatus 20 and received by mobile electronic device 116, in some embodiments, is unique for each patient support apparatus 20. That it, the resource(s) located at each URL are customized to the particular patient support apparatus 20 that is broadcasting the URL. Thus, for example, if a caregiver uses his or her device in the room 134 depicted in FIG. 5, when the caregiver walks to within the vicinity of first patient support apparatus 20, his or her mobile electronic device 116 receives a first URL 108 from patient support apparatus 20. When the caregiver walks to within the vicinity of the second patient support apparatus 20a, his or her mobile electronic device 116 receives a second URL 108a from second patient support apparatus 20a. The first URL 108 from the first patient support apparatus 20 provides mobile electronic device 116 with the resources and user interface to communicate with first patient support apparatus 20 and retrieve the data stored in first headwall unit 66, but does not give mobile electronic device 116 the resources and user interface to communicate with second patient support apparatus 20a and retrieve the data stored in second headwall unit 66a. Conversely, the second URL received from second patient support apparatus 20a provides mobile electronic device 116 with the resources and user interface to communicate with second patient support apparatus 20a and retrieve the data stored in second headwall unit 66a, but does not give mobile electronic device 116 the resources and user interface to communicate with first patient support apparatus 20 and retrieve the data stored in first headwall unit 66.

For some rooms, the patient support apparatuses 20 may be positioned sufficiently close together such that mobile electronic device 116 simultaneously detects two beacons, one from first patient support apparatus 20 and another from second patient support apparatus 20a. In such instances, mobile electronic device 116 receives two notifications, both of which uniquely identify the first and second patient support apparatuses 20 and 20a (such as, for example, by room number and bay area 102). The user can then select whichever one he or she wants, and mobile electronic device 116 responds by connecting to the URL associated with the chosen patient support apparatus 20 or 20a. If the user subsequently desires to switch to viewing the data associated with the other patient support apparatus, he or she can simply select the other notification on mobile electronic device 116 that corresponds to the other patient support apparatus 20. Selecting this other notification takes mobile electronic device 116 to the URL associated with that particular patient support apparatus. The user of mobile electronic device 116 can therefore easily switch back and forth between viewing and controlling the data associated with each of the patient support apparatuses 20 (and their respective patients, medical devices 112, and headwall units 66).

As was noted previously, the transmission of a URL to mobile electronic device 116 by patient support apparatus 20 may be used as an alternative manner of implementing the functionality described with respect to FIG. 6, or it may be used as a supplemental functionality, or it may be used independently and separately from the functionality of FIG. 6. When used as an alternative method, the URL received by mobile electronic device 116 directs mobile electronic device 116 to a resource that reads the preferred display settings stored on mobile electronic device 116 (or alternatively stored at the URL, or somewhere else accessible to the resources at the URL). The resource then uses the conventional web browsing software installed on mobile electronic device 116 to request the specific data identified in the user's preferences to be displayed in the format and on the display specified in the user's preferences.

When the transmission of the URL to mobile electronic device 116 is used as a supplement to the functionality of FIG. 6, mobile electronic device 116 automatically requests the user-preferred data stored in headwall unit 66 to be displayed in the user-preferred display in the user-preferred format. In addition to sending this request, the mobile electronic device 116 connects to the resources at the specified URL and allows the user to thereafter change and control any of the displayed data using the user interface specified by the URL and displayed on the conventional web browser on mobile electronic device 116.

When the transmission of the URL to mobile electronic device 116 is used separately from the functionality described with respect to FIG. 6, the URL provides the only means for mobile electronic device 116 to display, retrieve, sort, and otherwise control the display of data on the displays (62, 146, 158) within the room 134. In other words, the only requests for the headwall unit's data that are received from mobile electronic device 116 are generated using the functionality provided by the resources at the specified URL.

In summary, mobile electronic device 116 may be configured in at least three different manners for controlling the display, retrieval, sorting, and other aspects of the data. It can use methods described above with respect to FIG. 6 that utilize no URL; it can use both the methods described with respect to FIG. 6 and a URL; or it can use only the URL to control the display, retrieval, sorting, and other aspects of the data.

As was mentioned above, although FIG. 7 illustrates mobile electronic device 116 communicating directly with patient support apparatus 20 via communication link 160, it will be understood that this can be modified so that mobile electronic device 116 communicates directly with headwall unit 66 via a communication link 122. In such embodiments, mobile electronic device 116 operates in the same manner described above with the sole exception that communication takes place directly with headwall unit 66. Thus, in such embodiments, mobile electronic device 116 receives a URL 108 from headwall unit 66 that is unique to that particular headwall unit 66. The URL takes the mobile electronic device to a web resource that allows the user to control and interact with that particular headwall unit using an interface on the mobile electronic device's conventional web browser. The user can then use his or her mobile electronic device 116 to control what data associated with that particular headwall unit 66 is displayed in what locations within room 134 and in what format.

Figure 8:
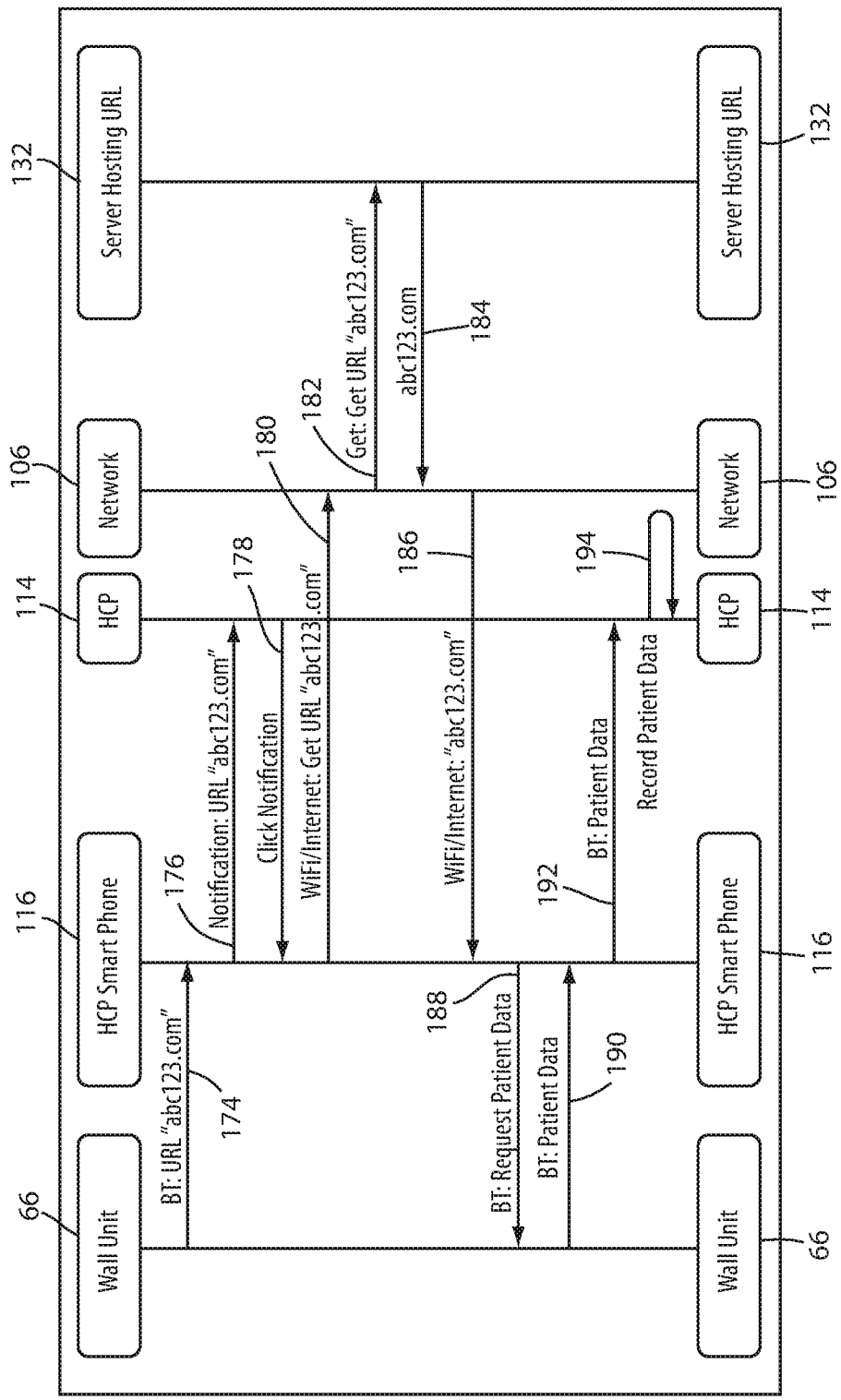
FIG. 8 is a sequence diagram illustrating one manner in which the URL may be forwarded to a mobile electronic device carried by a healthcare provider.

This alternative embodiment is illustrated in more detail in the sequence diagram shown in FIG. 8. As can be seen therein, headwall unit 66 repetitively broadcasts a URL beacon at step 174 using second transceiver 88. When mobile electronic device 116 is within range of headwall unit 66, it receives the URL message and displays a notification message at step 176 to the user of mobile electronic device 116 (e.g. caregiver 114). The user then has the option at step 178 of clicking, or otherwise activating the functionality associated with the notification. If and when the user activates this functionality, the mobile electronic device 116 connects to the URL specified in the message received at step 174. This connection takes place at step 180 where the mobile electronic device 116 uses its network transceiver (e.g. WiFi) to communicate with healthcare facility computer network 106. Healthcare network 106 then forwards the connection message to headwall server 132 at step 182, which, in this embodiment, hosts the location specified in the URL. As noted earlier, in other embodiments, the URL may be hosted at other locations.

In response to receiving the message at step 182, headwall server responds by sending the resources associated with the URL to network 106 at step 184. Network 106, in turn, forwards the resources to mobile electronic device 116 at step 186. Once received at mobile electronic device 116, the user is able to utilize the user interface displayed on the mobile electronic device 116 to request data from headwall unit 66. An example of such a request is shown at step 188 in FIG. 8. In response to the request, the requested data is sent at step 190 to the mobile electronic device 116. Mobile electronic device 116 then displays the requested data on its screen 158 at step 192. At an optional step 194, the user can enter data via mobile electronic device 116 that is then forwarded to headwall unit 66 for storage in memory 94 (or at another location where the data is stored).

Several variations of the sequence disclosed in FIG. 8 can be made. One such modification is that the request for data at step 188 can be modified so that the data request specifies a display other than display 158 of mobile electronic device 116. When such a modified request is sent to headwall unit 66 at step 188, headwall unit 66 responds at step 190 with the same data, but changes the intended recipient of the data. Thus, for example, instead of sending the requested data to mobile electronic device 116, headwall unit 66 sends the data to TV/display 62 and/or to controller 136 of patient support apparatus 20 for display on one or more displays 146.

The sequence of steps shown in FIG. 8 is also modified if the data received by headwall unit 66 from patient support apparatus 20 and its associated medical devices is stored at a different location, rather than memory 94. For example, in some embodiments, the data received from patient support apparatus 20 and its associated medical devices is stored at headwall server 132. In such instances, the URL transmitted at step 174 can be modified to specify the location of the stored data, rather than a resource that provides the programming needed to use the web browser of mobile electronic device 116 as a user interface for controlling communications with headwall unit 66 (or patient support apparatus 20). In such a modified embodiment, steps 176-186 may be omitted, and steps 188-190 are modified so that the request for data is transmitted, not to headwall unit 66, but instead to the URL identified in the message received at step 174. If the URL identifies headwall server 132, then the request for data at step 188 is sent to server 132 and server 132 responds at step 190 with the requested data.

When server 132 stores the data gathered by headwall unit 66 from its associated patient support apparatus 20 and medical devices 112, server 132 stores this data in a manner that separates the data associated with one headwall unit 66 from the data associated with other headwall units 66 of the medical facility. In some embodiments, the data is additionally or alternatively segregated by patient, patient support apparatus 20, medical devices 112, and/or by bay area 102. Such data separation ensures that when a mobile electronic device 116 requests data associated with a particular headwall unit 66, particular patient, particular patient support apparatus 20, and/or particular medical device 112, the data sent by server 132 is only data corresponding to that particular headwall unit 66, particular patient, particular patient support apparatus 20, and/or particular medical device 112. The data segregation, in some embodiments, is facilitated by having each headwall unit 66 and/or patient support apparatus 20 broadcast a unique URL that is different from URLs broadcasted by the other patient support apparatuses 20 and/or headwall units 66 within the healthcare facility.

Headwall system 156 may also include one or more security measures adapted to prevent unauthorized individuals from accessing the data stored in, or by, headwall unit 66. For example, in some embodiments, the URL may be encrypted with only authorized mobile electronic device 116 having the key for decrypting the URL. Additionally, or alternatively, headwall server 132 may include a list of authorized mobile electronic devices 116 that are authorized to receive data and/or resources such that non-authorized personnel, who may be in possession of the URL, are not able to download the resources and/or data stored at the URL. Still other security features may be incorporated into headwall system 156.

It will be understood by those skilled in the art that headwall system 156 may be modified in a variety of different manners. For example, in some embodiments, the URL sent by headwall unit 66 and/or patient support apparatus 20 is transmitted to the mobile electronic device 116 using near field communication (NFC). In such an embodiment, the user of mobile electronic device 116 moves his or her device 116 into close proximity to a designated location on patient support apparatus 20 and/or headwall unit 66. When in close proximity, the device transmits the corresponding URL to mobile electronic device 116 using any suitable near field communication protocol. The mobile electronic device 116 then uses the URL in any of the manners previously described. Examples of patient support apparatuses 20 including near field technology communication abilities that may be used to implement this modified embodiment of system 156 are disclosed in commonly assigned U.S. patent application Ser. No. 13/802,992 filed Mar. 14, 2013, by inventors Michael Hayes et al. and entitled COMMUNICATION SYSTEMS FOR PATIENT SUPPORT APPARATUSES, the complete disclosure of which is incorporated herein by reference. Other type of patient support apparatuses and/or NFC communication configurations may also be used.

As yet another modification, the URL may be conveyed to the mobile electronic device 116 using optical technology, such as, but not limited to, a Quick Response (QR) code, a bar code, or some other type of code that is recognizable by an image sensor (e.g. camera) that is part of mobile electronic device 116. Such codes are positioned at any suitable location on patient support apparatus 20, headwall unit 66, and/or headwall 54. After detecting and deciphering the code, mobile electronic device 116 uses the URL in any of the manners previously described.

Figure 9:
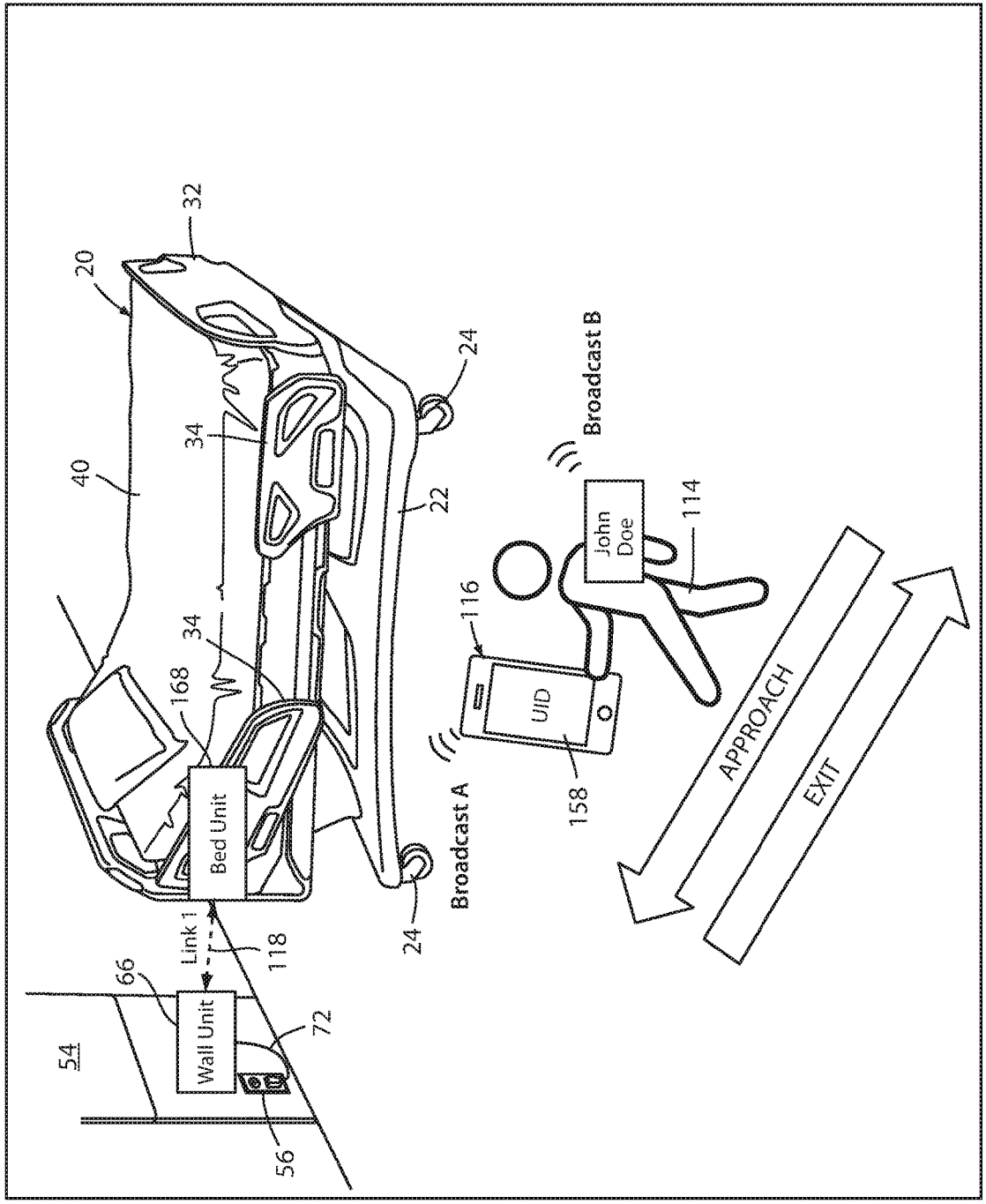
FIG. 9 is a perspective view of the headwall system of FIG. 4 showing one manner of implementing a healthcare worker detection subsystem.

FIG. 9 illustrates one manner in which headwall system 156 can be configured to automatically detect the approach of a healthcare worker 114. Mobile electronic device 116 is configured to repetitively emit a beacon signal using a protocol detectable by second transceiver 88 of headwall unit 66 and/or second transceiver 140 of patient support apparatus 20 (e.g. a Bluetooth transceiver). After detecting this beacon signal, controller 92 of headwall unit 66 and/or controller 136 of patient support apparatus 20 determine whether the healthcare worker is approaching and/or leaving the room 134 utilizing any one or more of the following techniques: using signal triangulation of the beacon signals with other headwall units 66 and/or other patient support apparatuses 20; monitoring the value and rate of change of the received signal strength indicators (RSSI) in the messages; using one or more directional antennas on headwall unit 66 and/or patient support apparatus 20; and/or communicating with an app on the mobile electronic device 116 that detects and shares movement and/or location information of the mobile electronic device 116. Alternatively, or additionally, caregiver 114 may wear a badge or other electronic device that is detectable by caregiver presence detector 98 of headwall unit 66.

Figure 10:
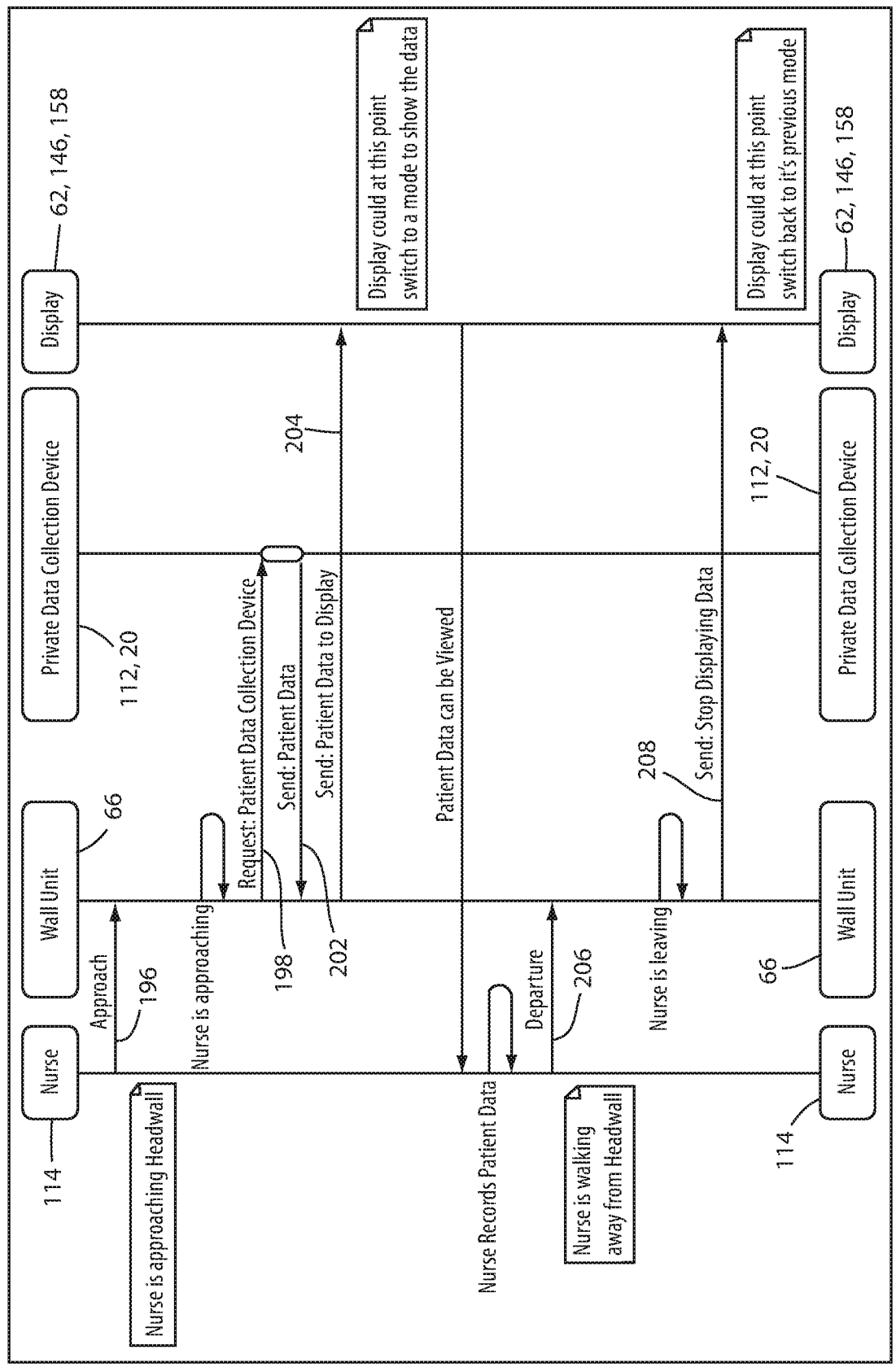
FIG. 10 is a sequence diagram illustrating a data refresh feature of the headwall system of FIG. 4.

FIG. 10 illustrate a sequencing diagram illustrating one manner of implementing an automatic data refresh feature and an automatic data removal feature of headwall system 156. The sequencing diagram utilizes the automatic caregiver detection feature discussed above with respect to FIG. 9. At an initial step 196, a caregiver approaches the bay area 102 and this is detected by headwall unit 66 and/or patient support apparatus 20 (either one, or both of these, may include the caregiver detection functionality discussed above). In response to detecting this caregiver approach, headwall unit 66 automatically sends out a request at step 198 for the latest data from one or more medical devices. The medical devices include both patient support apparatus 20 and any non-patient support apparatus medical devices 112 that are associated with the patient in patient support apparatus 20. The medical devices (20 and/or 112) respond to this request by sending the latest updates of the requested information at step 202. Upon receiving the latest data from the medical devices, controller 92 of headwall unit 66 sends the data at step 204 to one or more default displays (62, 146, 158), to one or more displays indicated in the users preferences (saved on mobile electronic device 116 and transmitted to headwall unit 66), or to one or more displays indicated by the user's interactions with mobile electronic device 116 after the device has connected to the URL transmitted by headwall unit 66 and/or patient support apparatus 20.

After the latest data is displayed on the corresponding display(s) 62, 146, and/or 158, headwall system 156 may implement an automatic data removal feature when the caregiver exits the room 134, thereby preventing the data from being seen by unauthorized individuals. Steps 206-208 illustrate this feature. At step 206, either or both of controllers 92 and 136 detect that the caregiver 114 is leaving the room, using any of the methods discussed above with respect to FIG. 9. Upon detecting that the caregiver is exiting the room 134, or has exited the room, controller 92 of headwall unit 66 sends a message to the various display(s) 62, 146, and/or 158 instructing them to stop displaying the data previously displayed. Not only does this help prevent the data from being seen by unauthorized individuals, it also allows TV/display 62 to return to being used as a television, and allows patient support apparatus display 146 to return to displaying its normal information, rather than the data from headwall unit 66. In some embodiments, controller 92 may omit sending a command to mobile electronic device 116 to stop displaying the data because the caregiver 114 can manually clear the screen when he or she desires.

Figure 11:
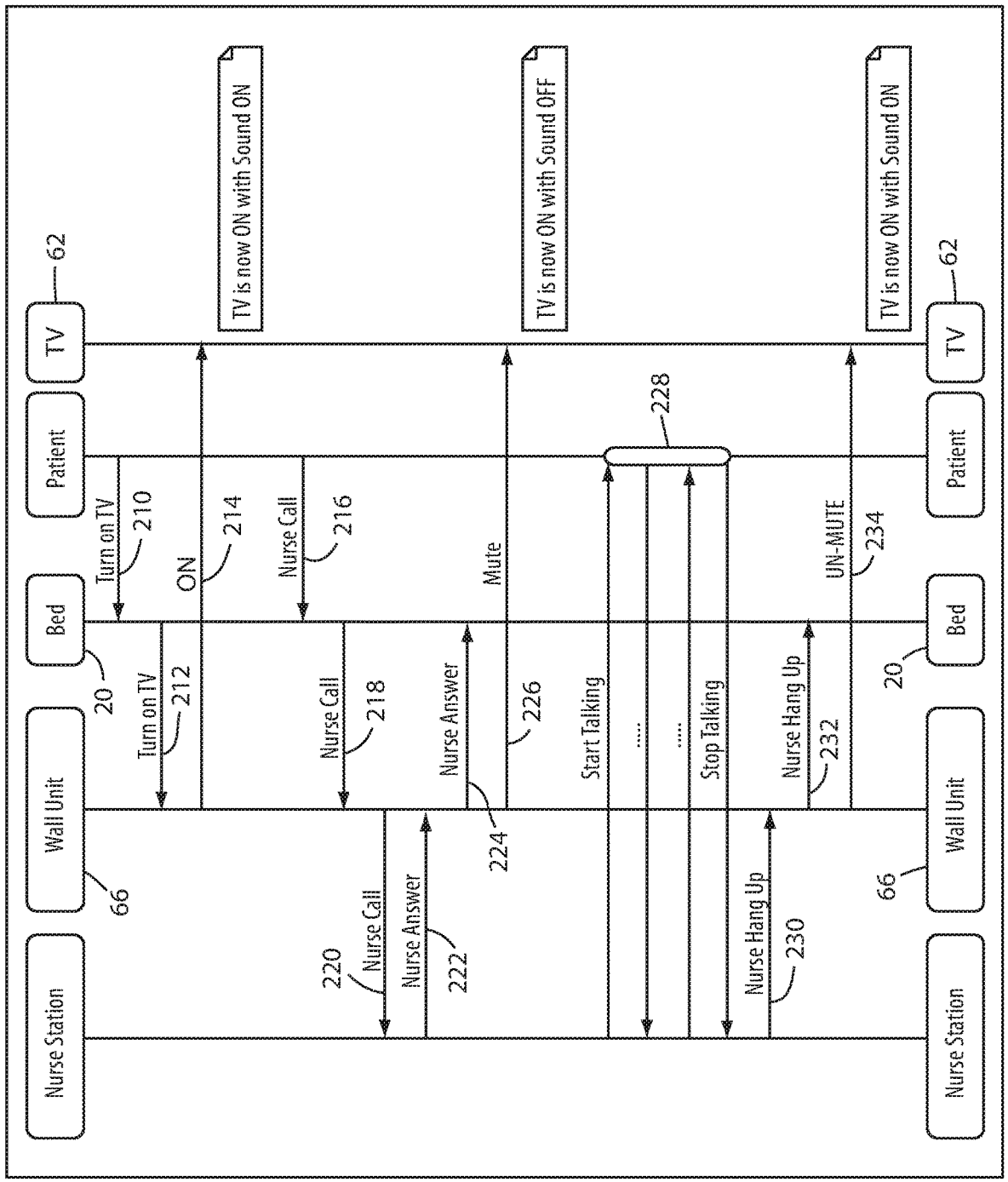
FIG. 11 is a sequence diagram illustrating an automatic volume control feature of the headwall system of FIG. 4.

FIG. 11 illustrates an automatic silencing/muting feature that may be included with headwall system 156, or that may be implemented separately from headwall system 156. This feature acts to automatically mute, or reduce the volume of, television/display 62 and/or radios positioned within the room 134 when the patient is communicating with a remotely positioned caregiver (e.g. at a nurses' station) via nurse call system 60. The feature is implemented starting at a step 210 when a patient on patient support apparatus 20 sends a command to turn on the TV/display 62 by manipulating a conventional television control on patient support apparatus 20. Patient support apparatus 20 responds to this patient-action by sending at step 212 a TV turn-on command to headwall unit 66 over communication link 118 (or, in some embodiments, communication link 128). Headwall unit 66 forwards this command to the TV/display 62 at step 214. In one embodiment, the forwarding step 214 takes place by sending the command to cable port 56 and room interface board 58, which then forwards the command to TV/display 62. In another embodiment, headwall unit 66 includes a wireless transceiver that communicates directly with a similar-type wireless transceiver built into, or added to (e.g. via a wireless transceiver dongle), TV/display 62. In either embodiment, TV/display 62 turns on in response to the command.

At any point in time while TV/display 62 is turned on, the patient may initiate a call to a remote caregiver via a nurse call control on patient support apparatus 20, or the caregiver may initiate a call to the patient remotely from the nurses' station. In either situation, headwall unit 66 detects this and automatically mutes or turns down the volume of TV/display 62. In example shown in FIG. 11, the patient is shown to initiate a call to a remote nurse at step 216. This is performed by activating a nurse call button, or other control, on patient support apparatus 20. In response to this activation, controller 136 of patient support apparatus 20 forwards a nurse call signal at step 218 to headwall unit 66 via communication link 118 (or, in some embodiments, communication link 128). In response to the receipt of this nurse call signal, headwall unit 66 forwards the nurse call signal at step 220 to nurse call system 60, which in turn forwards the nurse call signal to a nurses' station. This forwarding of the nurse call signal takes place via cable 72, cable port 56 and room interface board 58.

If and when a nurse at the nurses' station answer the call, the nurses' station forwards a nurse answer signal back to headwall unit 66 at step 222. The nurse answer signal is forwarded through room interface board 58, cable port 56, and cable 72 to headwall unit 66. Headwall unit 66 forwards the nurse answer signal to patient support apparatus 20 at step 224 (e.g. via link 118, or in some embodiments, link 128). Headwall unit 66 also forwards a volume or mute command to TV/display 62 at step 226 at or near the time it carries out step 224. As with all the commands to TV/display 62, controller 92 of headwall unit 66 forwards these either via room interface board or, if TV/display 62 includes a wireless transceiver, via one of the wireless transceivers of headwall unit 66. TV/display 62 either completely turns its sound off, or drops the sound level to a suitable sound level in response to the volume command at step 226.

During time period 228 (FIG. 11), audio signals are passed back and forth between the patient and the remote nurse. These audio signals pass through headwall unit 66 and headwall unit 66 forwards them back and forward between patient support apparatus 20 and nurse call system 60 as appropriate. During time period 228, the sound from TV/display 62 is muted or sufficiently reduced such that the conversation between the patient and the remote nurse does not suffer from aural interference due to sounds emanating from TV/display 62. When the time comes for the patient and nurse to end their conversation, either the nurse of the patient hangs up and the audio connection is terminated. In the example of FIG. 11, this audio disconnection is shown as originating from the nurse (steps 230 and 232), but it will be understood that the audio connection can also be terminated by the patient from patient support apparatus 20. In either case, headwall unit 66 automatically sends another volume command to TV/display 62 at step 234 that unmutes the sound from TV/display 62, or that otherwise returns the volume level of the TV/display 62 to its volume level prior to the nurse-patient communications.

Although FIG. 11 depicts an automatic sound reduction of TV/display 62 during nurse-patient communications, it will be understood that this feature can be extended to radios and/or any other sound-emitting devices that are either in communication with room interface board 58, or that have wireless transceivers compatible with at least one of the wireless transceivers contained within headwall unit 66. Thus, for example, if a patient is listening to a radio instead of watching TV/display 62 and he or she has a conversation with a remotely positioned nurse, headwall unit 66 will automatically turn down the volume of the radio during the nurse-patient communication so that the sound does not interfere with the conversation. Headwall unit 66 will also automatically restore the volume of the radio to its previous level when the call with the nurse terminates.

Figure 12:
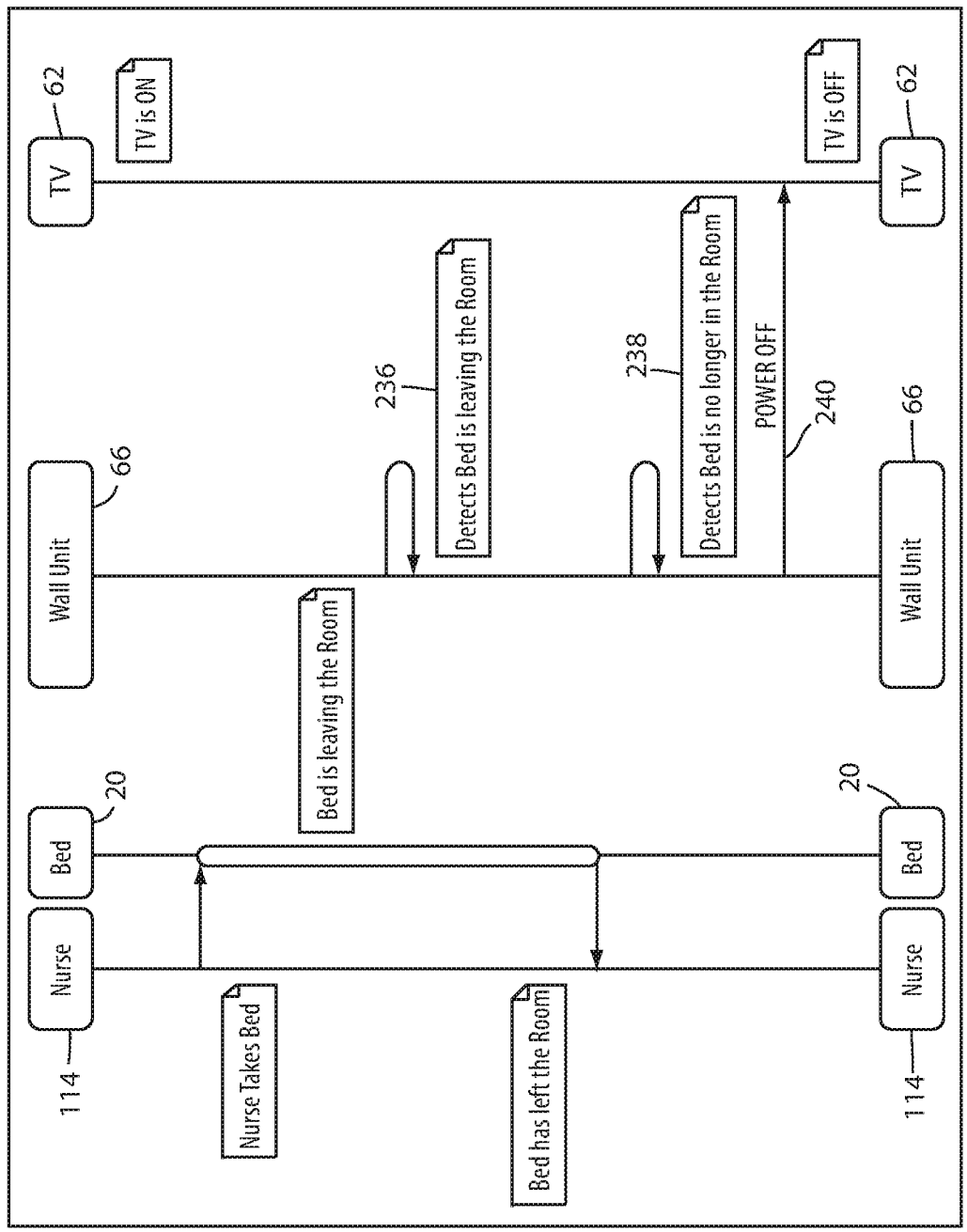
FIG. 12 is a sequence diagram illustrating an automatic entertainment device shut-off feature of the headwall system of FIG. 4.

FIG. 12 illustrates an automatic shut off feature that may be included with headwall system 156, or that may be implemented separately from headwall system 156. This feature acts to automatically shut off television/display 62 and/or radios positioned within the room 134 when the patient support apparatus 20 is moved out of the room 134. Headwall unit 66 implements this feature by detecting at steps 236 and 238 that patient support apparatus 20 is leaving the room 134 and/or has left room 134. Headwall unit 66 can be configured to detect either or both of these actions in a variety of different manners. In one embodiment, patient support apparatus 20 is configured to send a message to headwall unit 66 when it detects it is in motion, or has its brake deactivated, or is changing position. This message informs controller 92 of headwall unit 66 that the patient support apparatus is in the process of leaving. Further, if patient support apparatus 20 does not transmit a subsequent message for a minimum amount of time (indicating that it has likely stopped moving or that the brake has been re-activated) or if patient support apparatus 20 stops communicating with headwall unit 66 (because it has likely moved out of range of first and second transceivers 86 and 88 of headwall unit 66), controller 92 concludes that patient support apparatus 20 has left the room 134.

In still another embodiment, headwall unit 66 may—after losing communication with patient support apparatus 20 via first and second transceiver 86 and 88—send a message to patient support apparatus 20 via a longer range transceiver (e.g. network transceiver 90) and query if it has detected movement, and use the reply to conclude that patient support apparatus 20 has left the room. Any of the methods disclosed in commonly assigned U.S. provisional patent application Ser. No. 62/587,867 filed Nov. 17, 2017, by inventors Alex Bodurka et al. and entitled PATIENT SUPPORT APPARATUSES WITH LOCATION/MOVEMENT DETECTION, may also be used by headwall unit 66 to determine when patient support apparatus 20 is leaving, or has left, room 134. The complete disclosure of this patent application is incorporated herein by reference. Still other methods may be used for detecting the departure of patient support apparatus 20 from room 134 and/or its absence in room 134.

Regardless of the specific method used to detect the departure of patient support apparatus 20 from room 134, controller 92 of headwall unit 66 automatically sends a command at step 240 to TV/display 62 instructing it to turn off. The caregiver therefore doesn't have to remember to shut off the television, and both unnecessary energy consumption and unwanted sounds are reduced through this automatic action of headwall unit 66.

Figure 13:
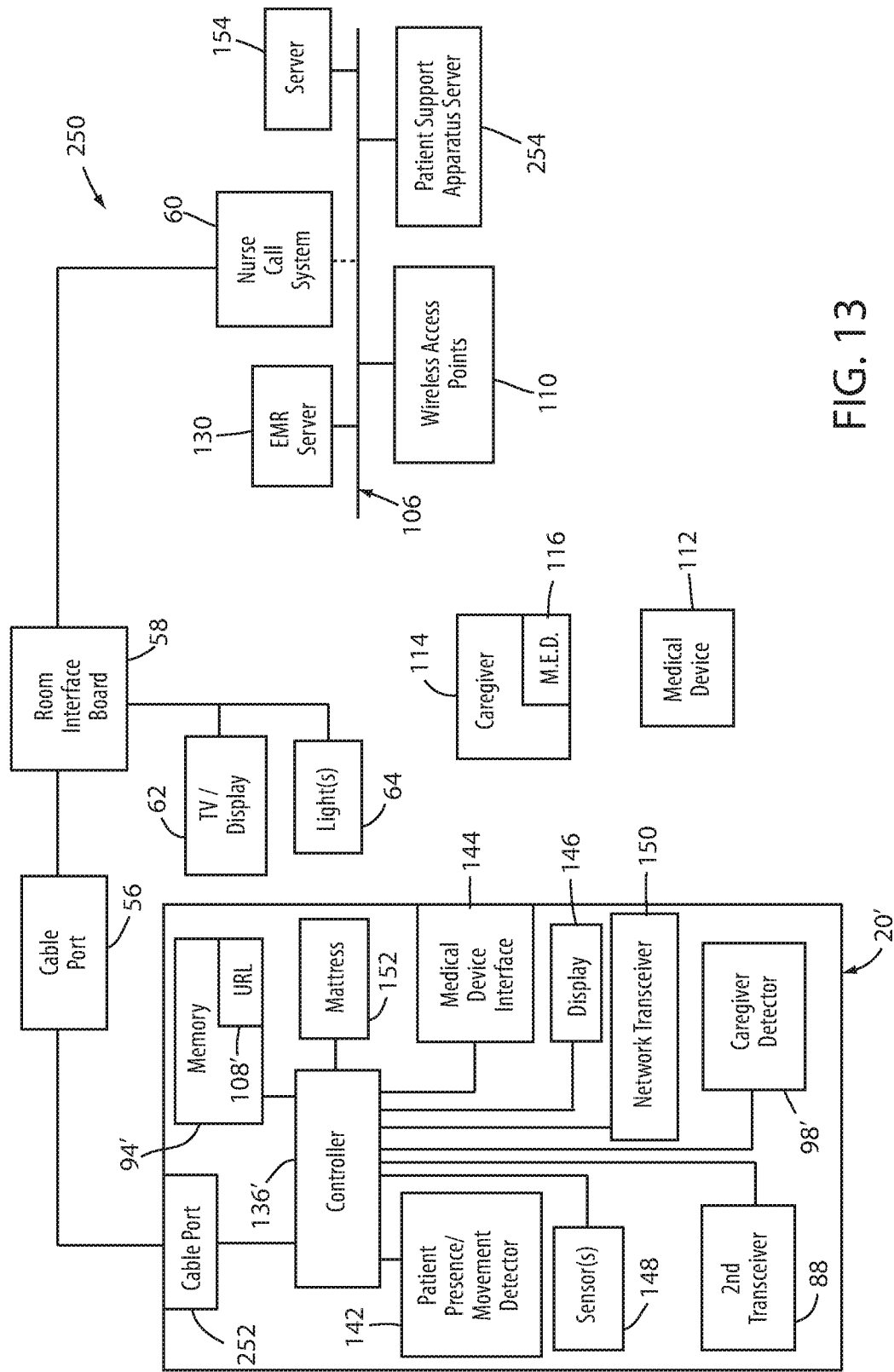
FIG. 13 is a block diagram of an alternative patient support apparatus into which various features of the headwall system of FIG. 4 are incorporated.

FIG. 13 depicts a patient support apparatus system 250 according to another embodiment of the present disclosure. Patient support apparatus system 250 includes a number of components that are also found in headwall system 156 and that operate in the same manner. These components are provided with the same reference numbers in patient support apparatus system 250. Patient support apparatus system 250 also includes a number of components that are similar to components of headwall system 156 but that have been modified in some manner. These components are labeled with the same number with a prime symbol (') added thereafter. Those components that are new are labeled with a new reference number.

Patient support apparatus system 250 provides any one or more of the above-described functions of headwall system 156, but does so by moving the non-nurse-call functionality of headwall unit 66 to a patient support apparatus 20'. In other words, headwall unit 66 is eliminated from patient support apparatus system 250 and its memory 94 (and URL 108), caregiver detector 98, and, in some cases (not shown), its auxiliary transceiver 96, are moved to patient support apparatus 20'. Further, the functions carried out by controller 92 of headwall unit 66 are shifted to controller 136 of patient support apparatus 20', and headwall unit 66 is replaced by a conventional nurse-call cable coupled between a cable port 252 on patient support apparatus 20' and cable port 56. Patient support apparatus 20' communicates with room interface board 58 and its associated components (nurse call system 60, TV/display 62, room lights 64, etc.) using conventional structures.

Instead of storing data within memory 94 of headwall unit 66 (or another location controlled by controller 92 of headwall unit 66), patient support apparatus system 250 stores the same data within a memory 94' positioned on board patient support apparatus 20', or at a location controlled by controller 136' of patient support apparatus 20'. This stored data includes any of the stored data discussed above with respect to headwall system 156, including data communicated to patient support apparatus 20' (via medical device interface 144) from one or more medical devices 112, as well as data that originates from patient support apparatus 20' itself (e.g. from sensors 148 or other sources). Controller 136' of patient support apparatus 20' processes this data in the same manners discussed above with respect to headwall system 156. This includes displaying the data on one or more displays (62, 146, and/or 158) within the room 134, either automatically in response to detecting caregiver 114 (or his/her mobile electronic device 116) or in response to the caregiver 114 manipulating his or her mobile electronic device 116 and manually instructing patient support apparatus 20' to display the data.

Patient support apparatus 20' is also adapted to utilize second transceiver 140 as a beacon to broadcast URL 108' to nearby mobile electronic device 116. URL 108' takes the mobile electronic device 116 to a location that either provides the resources and user interface to the web browser of mobile electronic device 116 to enable the caregiver to interact with patient support apparatus 20' (including controlling the display of the data stored in memory 94'), or to a location that stores the data, such as, but not limited to, a patient support apparatus server 254. Controller 136' of patient support apparatus 20' is also adapted to perform any of the features discussed above with respect to headwall system 156, such as, but not limited to: automatically detecting the presence of caregiver 114 and/or his or her mobile electronic device 116; automatically refreshing data readings when caregiver 114 enters room 134; automatically detecting movement of patient support apparatus 20' into or out of a room 134; automatically muting the sound from TV/display 62 (or other sound-emitting devices) during a patient's conversation with a remotely positioned caregiver; and automatically shutting off the TV/display 62 (or other electronic devices) when patient support apparatus 20' leaves the room.

Although patient support apparatus 20' is not shown in FIG. 13 as including first transceiver 86, it will be understood that patient support apparatus 20' can be modified to include first transceiver 86. When so modified, first transceiver 86 allows patient support apparatus 20' to communicate with first units 68 that are positioned in fixed locations within each room and/or bay area 102 (second units 70 are not included). Patient support apparatus 20' communicates with first units 68 in order to determine its location within healthcare facility. If neither first units 68 nor first transceiver 86 are included in a particular setting, patient support apparatus 20' may be adapted to determine its location in another manner. For example, in some embodiments, patient support apparatus 20' is configured to determine its location using triangulation and/or trilateration with respect to the known position of the multiple access points 110. Examples of patient support apparatuses configured to perform this type of location detection are disclosed in commonly assigned U.S. patent application Ser. No. 14/559,458 filed Dec. 3, 2014, by inventors Michael Hayes et al. and entitled PATIENT SUPPORT APPARATUS COMMUNICATION SYSTEMS, the complete disclosure of which is incorporated herein by reference. Other types of location-detection systems may also be utilized with patient support apparatus 20'.

It will be understood that various modifications may be made to the structures and methods of both headwall system 156 and/or patient support apparatus system 250 described herein. For example, although headwall unit 66 has been described in headwall system 156 as comprising first and second wall units 68 and 70, it will be understood that neither headwall unit 66 itself nor its component units 68 and 70 need to be mounted to a wall. Instead, headwall unit 66 and/or its component units 68 and/or 70 can be mounted in any fixed location within a room, including, but not limited to, the ceiling, the floor, or to other architectural structures within the room. This is also true for first wall unit 68 in those embodiments of patient support apparatus system 250 that utilize first wall units 68.

It will also be understood that controller 136 and/or controller 136' may be modified to communicate with nurse call system 60 via network transceiver 150 in addition to such communication via cable port 56. Communicating via network transceiver 150 can be useful in situations where patient support apparatus 20 (or 20') has been moved out of a room and is no longer in communication with the headwall unit 66 and/or has been disconnected from cable port 56. By communicating using network transceiver 150, controller 136 (or 136') is able to send a message to the nurse call system 60 (via access points 110) indicating that it has moved away from headwall unit 66 and/or bay area 102, and the nurse call system 60 can therefore cancel any cord-out alerts that may otherwise have been instituted and/or take other actions knowing that patient support apparatus 20, 20' is no longer positioned at that particular bay area 102.

It will also be understood that the use of the term "transceiver" herein is intended to cover not only devices that include a transmitter and receiver contained within a single unit, but also devices having a transmitter separate from a receiver, and/or any other devices that are capable of both transmitting and receiving signals or messages.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A stationary communication unit adapted to be mounted in a room of a healthcare facility, the stationary communication unit comprising:
   a radio frequency (RF) transceiver adapted to directly and wirelessly communicate audio signals to and from a patient support apparatus;
   an infrared transceiver adapted to directly and wirelessly transmit a location signal to the patient support apparatus;
   a wired transceiver adapted to directly communicate with a nurse call system port installed on a wall of the room, the nurse call system including a plurality of pins;
   a fourth transceiver adapted to directly and wirelessly communicate with a medical device positioned in the room, the medical device being different from the patient support apparatus; and
   a controller adapted to forward the audio signals received by the RF transceiver from the patient support apparatus to the wired transceiver for forwarding to a particular pin of the plurality of pins.

2. The stationary communication unit of claim 1 wherein the RF transceiver is a Bluetooth transceiver.

3. The stationary communication unit of claim 1 wherein the RF transceiver is further adapted to receive a request to communicate with a caregiver when the caregiver is remotely located, the request being initiated by a patient supported on the patient support apparatus, and wherein the controller is further adapted to forward the request to the nurse call system port via the wired transceiver.

4. The stationary communication unit of claim 1 wherein the controller is adapted to receive data from the medical device via the fourth transceiver and to forward it to a server within the healthcare facility.

5. The stationary communication unit of claim 1 wherein the controller is adapted to receive data from the medical device and store the data from the medical device in a memory contained within the stationary communication unit, and the controller is further adapted to receive a request for the data from the medical device from a requesting device positioned in the room and to transmit the data from the medical device to the requesting device in response thereto.

6. The stationary communication unit of claim 1 wherein the controller is further adapted to use the infrared transceiver to detect when the patient support apparatus is present in the room and when the patient support apparatus is not present in the room, the controller also adapted to communicate with an entertainment device positioned in the room and to automatically send a command to the entertainment device in response to detecting that the patient support apparatus is not present in the room, the command instructing the entertainment device to do at least one of the following: (1) turn off, or (2) reduce a volume of sound emitted from the entertainment device.

7. The stationary communication unit of claim 1 further comprising a caregiver presence detection subsystem, the caregiver presence detection subsystem adapted to detect when a caregiver is present in the room and when the caregiver is not present in the room, the caregiver presence detection subsystem detecting a presence of the caregiver by communicating with a mobile device carried by the caregiver, the mobile device including a unique identifier and a transceiver adapted to communicate the unique identifier to the controller when the mobile device is positioned within the room.

8. The stationary communication unit of claim 7 wherein the controller is further adapted to transmit a uniform resource locator (URL) to a mobile device carried by the caregiver when the caregiver is in the room, the URL identifying a location where the data from the medical device is stored, the location being accessible to the mobile device using conventional web browsing software installed on the mobile device.

9. The stationary communication unit of claim 3 wherein the controller is in communication with an entertainment device positioned in the room, and the controller is adapted to automatically send a volume change command to the entertainment device in response to the request to communicate with the caregiver.

10. The stationary communication unit of claim 7 wherein the controller is further adapted to transmit a uniform resource locator (URL) to a mobile device carried by the caregiver when the caregiver is in the room, the URL identifying a location where the data from the medical device is stored, and the controller is further adapted to receive data from multiple medical devices positioned in the room and to store the data received from the multiple medical devices at the location identified by the URL.

11. A stationary communication unit adapted to be mounted in a room of a healthcare facility, the stationary communication unit comprising:
    a first transceiver adapted to communicate with a patient support apparatus and receive a request to communicate with a caregiver when the caregiver is remotely located, the request initiated by a patient supported on the patient support apparatus;
    a second transceiver in communication with a nurse call system port, the nurse call system port installed on a wall of a room in which the stationary communication unit is mounted;
    a caregiver presence detection subsystem, the caregiver presence detection subsystem adapted to detect when the caregiver is present in the room and when the caregiver is not present in the room; and
    a controller adapted to forward the request to the nurse call system port via the second transceiver, the controller also adapted to automatically send data to a display positioned in the room in response to detecting a presence of the caregiver in the room.

12. The stationary communication unit of claim 11 wherein the display is positioned on the patient support apparatus.

13. The stationary communication unit of claim 11 wherein the display is located on a mobile device carried by the caregiver.

14. The stationary communication unit of claim 11 wherein the data is received by the controller from multiple medical devices positioned in the room.

15. The stationary communication unit of claim 14 wherein the data is received through the first transceiver.

16. The stationary communication unit of claim 15 wherein the data from the multiple medical devices includes data generated from one or more sensors of the multiple medical devices.

17. The stationary communication unit of claim 11 wherein the caregiver presence detection subsystem detects a presence of the caregiver by communicating with a mobile device carried by the caregiver, the mobile device including a unique identifier and a transceiver adapted to communicate the unique identifier to the controller when the mobile device is positioned within the room.

18. The stationary communication unit of claim 17 wherein the controller is further adapted to transmit a uniform resource locator (URL) to the mobile device when the caregiver is in the room, the URL identifying a location where the data is stored, the location being accessible to the mobile device using conventional web browsing software installed on the mobile device such that the data may be displayed on the display.

19. The stationary communication unit of claim 11 further comprising a patient support apparatus presence detection subsystem, the patient support apparatus presence detection subsystem adapted to detect when the patient support apparatus is present in the room and when the patient support apparatus is not present in the room, and wherein the controller is adapted to communicate with an entertainment device positioned in the room and to automatically send a command to the entertainment device in response to detecting that the patient support apparatus is not present in the room, the command instructing the entertainment device to do at least one of the following: (1) turn off, and (2) reduce a volume of sound emitted from the entertainment device.

20. The stationary communication unit of claim 11 wherein the data comes from a medical device positioned in the room and the controller is adapted to receive updated data from the medical device while the caregiver is in the room, the controller further adapted to send the updated data to the display while the caregiver is in the room.

* * * * *